United States Patent
Palomino Laria et al.

(10) Patent No.: US 11,872,226 B2
(45) Date of Patent: Jan. 16, 2024

(54) N-BENZYL-2-PHENOXYBENZAMIDE DERIVATIVES AS PROSTAGLANDIN E2 (PGE2) RECEPTORS MODULATORS

(71) Applicant: MEDIBIOFARMA, S.L., Navarra (ES)

(72) Inventors: Julio Castro Palomino Laria, Barcelona (ES); Juan Camacho Gómez, Barcelona (ES); Rodolfo Rodríguez Iglesias, Navarra (ES); Irene Velilla Martínez, Navarra (ES)

(73) Assignee: MEDIBIOFARMA, S.L., Navarra (ES)

( * ) Notice: Subject to any disclaimer, the term of this patent is extended or adjusted under 35 U.S.C. 154(b) by 176 days.

(21) Appl. No.: 17/310,512

(22) PCT Filed: Feb. 7, 2020

(86) PCT No.: PCT/EP2020/053069
§ 371 (c)(1),
(2) Date: Aug. 6, 2021

(87) PCT Pub. No.: WO2020/161275
PCT Pub. Date: Aug. 13, 2020

(65) Prior Publication Data
US 2022/0117962 A1  Apr. 21, 2022

(30) Foreign Application Priority Data
Feb. 8, 2019 (EP) .................... 19382088

(51) Int. Cl.
| | | |
|---|---|---|
| *A61K 31/505* | (2006.01) | |
| *A61K 31/195* | (2006.01) | |
| *A61K 31/277* | (2006.01) | |
| *A61K 31/341* | (2006.01) | |
| *A61K 31/381* | (2006.01) | |
| *A61K 31/415* | (2006.01) | |
| *A61K 31/4418* | (2006.01) | |
| *C07C 233/76* | (2006.01) | |
| *C07C 255/59* | (2006.01) | |
| *C07D 213/56* | (2006.01) | |
| *C07D 231/12* | (2006.01) | |
| *C07D 239/26* | (2006.01) | |
| *C07D 307/58* | (2006.01) | |
| *C07D 333/24* | (2006.01) | |

(52) U.S. Cl.
CPC .......... *A61K 31/505* (2013.01); *A61K 31/195* (2013.01); *A61K 31/277* (2013.01); *A61K 31/341* (2013.01); *A61K 31/381* (2013.01); *A61K 31/415* (2013.01); *A61K 31/4418* (2013.01); *C07C 233/76* (2013.01); *C07C 255/59* (2013.01); *C07D 213/56* (2013.01); *C07D 231/12* (2013.01); *C07D 239/26* (2013.01); *C07D 307/58* (2013.01); *C07D 333/24* (2013.01)

(58) Field of Classification Search
CPC .. C07C 233/76; A61K 31/381; A61K 31/341; A61K 31/277; A61K 31/195; A61K 31/505
See application file for complete search history.

(56) References Cited

FOREIGN PATENT DOCUMENTS

| WO | 2005021508 A1 | 3/2005 |
| WO | 2011094231 A1 | 8/2011 |
| WO | 2017085198 A1 | 5/2017 |

OTHER PUBLICATIONS

Xia et al., "Prostaglandin E2 promotes the cell growth and invasive ability of hepatocellular carcinoma cells by upregulating c-Myc expression via EP4 receptor and the PKA signaling pathway", Oncology Reports, vol. 32, pp. 1521-1530, 2014.
Xu et al., "An EP4 Antagonist ONO-AE3-208 Suppresses Cell Invasion, Migration, and Metastasis of Prostate Cancer", Cell Biochemistry and Biophysics, vol. 70, pp. 521-527, 2014.
Yao et al., "Prostaglandin E2-EP4 signaling promotes immune inflammation through TH1 cell differentiation and TH17 cell expansion", Nature Medicine, vol. 15, No. 6, pp. 633-641, Jun. 2009.
Yokoyama et al., "Inhibition of EP4 Signaling Attenuates Aortic Aneurysm Formation", PLOS ONE, vol. 7, Issue 5, e36724, pp. 1-10, May 2012.

(Continued)

*Primary Examiner* — Marcos L Sznaidman
(74) *Attorney, Agent, or Firm* — McKee, Voorhees & Sease, PLC

(57) ABSTRACT

The present invention relates to novel, optionally substituted, N-benzyl-2-phenoxybenzamide derivatives of formula (I), as modulators of EP4 and/or EP2 receptors of prostaglandin E2 (PGE2), to processes for their preparation, to pharmaceutical compositions comprising said compounds and to said compound for use in the treatment of pathological conditions, disorders or diseases that can improve by modulation of EP4 and/or EP2 receptors of prostaglandin E2 (PGE2) such as cancer disease, pain, inflammation, neurodegenerative diseases and kidney diseases.

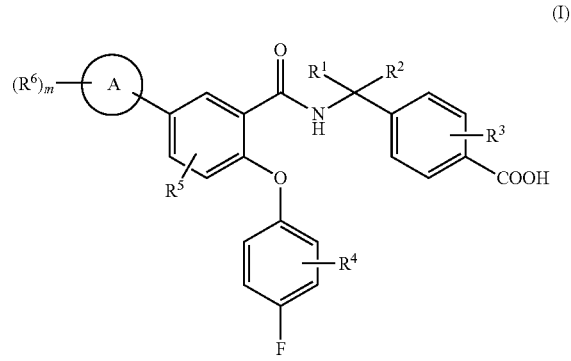

15 Claims, No Drawings

(56) References Cited

OTHER PUBLICATIONS

Yokoyama et al., "The Prostanoid EP4 Receptor and Its Signaling Pathway", Pharmacological Reviews, vol. 65, pp. 1010-1052, Jul. 2013.
Zang et al., "PGE2-synthesis and signaling in malignant transformation and progression of human hepatocellular carcinoma", Human Pathology, vol. 63, doi: 10.1016/j.humpath.2017.02.018, pp. 1-42, May 2017.
Zhang et al., "Prostaglandin E2 receptor 4 mediates renal cell carcinoma intravasation and metastasis", Cancer Letters, pp. 1-9, 2017.
Wilson et al., "GW627368X ((N-{2-[4-(4,9-diethoxy-1-oxo-1,3-dihydro-2H-benzo[f]isoindol-2-yl)phenyl]acetyl} benzene sulphonamide): a novel, potent and selective prostanoid EP4 receptor antagonist", British Journal of Pharmacology, vol. 148, pp. 326-339, 2006.
Abramovitz et al., "The utilization of recombinant prostanoid receptors to determine the affinities and selectivities of prostaglandins and related analogs", Biochimica et Biophysica Acta 1483, pp. 285-293, 2000.
Albu et al., "EP4 Antagonism by E7046 diminishes Myeloid immunosuppression and synergizes with Treg-reducing IL-2-Diphtheria toxin fusion protein in restoring anti-tumor immunity", Oncoimmunology, vol. 6, No. 8, pp. e1338239-1-e1338239-14, 2017.
Aoki et al., "Prostaglandin E2-EP2 signaling as a node of chronic inflammation in the colon tumor microenvironment", Aoki and Narumiya Inflammation and Regeneration, vol. 37, No. 4, DOI 10.1186/s41232-017-0036-7, pp. 1-5, 2017.
Aringer et al., "Blockade of prostaglandin E2 receptor 4 ameliorates nephrotoxic serum nephritis", Am J Physiol Renal Physiol, vol. 315, pp. F1869-F1880, 2018.
Arosh et al., "Molecular and preclinical basis to inhibit PGE2 receptors EP2 and EP4 as a novel nonsteroidal therapy for endometriosis", PNAS, vol. 112, No. 31, pp. 9716-9721, Aug. 4, 2015.
Attur et al., "Prostaglandin E2 Exerts Catabolic Effects in Osteoarthritis Cartilage: Evidence for Signaling via the EP4 Receptor1", The Journal of Immunology, http://www.jimmunol.org/content/181/7/5082, pp. 1-8, downloaded Dec. 16, 2014.
Audoly et al., "Substitution of Charged Amino Acid Residues in Transmembrane Regions 6 and 7 Affect Ligand Binding and Signal Transduction of the Prostaglandin EP3 Receptor", Molecular Pharmacology, vol. 51, pp. 61-68, 1997.
Banu et al., "Selective Inhibition of Prostaglandin E2 Receptors EP2 and EP4 Induces Apoptosis of Human Endometriotic Cells through Suppression of ERK1/2, AKT, Nfkb, and β-Catenin Pathways and Activation of Intrinsic Apoptotic Mechanisms", Mol Endocrinol, vol. 23, No. 8, pp. 1291-1305, Aug. 2009.
Bäurle et al., "Identification of a Benzimidazolecarboxylic Acid Derivative (BAY 1316957) as a Potent and Selective Human Prostaglandin E2 Receptor Subtype 4 (hEP4-R) Antagonist for the Treatment of Endometriosis", Journal of Medicinal Chemistry, vol. 62, pp. 2541-2563, 2019.
Chang et al., "Role of prostaglandin E2-dependent angiogenic switch in cyclooxygenase 2-induced breast cancer progression", PNAS, vol. 101, No. 2, pp. 591-596, Jan. 13, 2004.
Chen et al., "A novel antagonist of the prostaglandin E2 EP4 receptor inhibits Th1 differentiation and Th17 expansion and is orally active in arthritis models", British Journal of Pharmacology, vol. 160, pp. 292-310, 2010.
Cheng et al., "Prostaglandin E2 receptor EP2 mediates Snail expression in hepatocellular carcinoma cells", Oncology Reports, vol. 31, pp. 2099-2106, 2014.
De Keijzer et al., "The Multiple Faces of Prostaglandin E2 G-Protein Coupled Receptor Signaling during the Dendritic Cell Life Cycle", Int. J. Mol. Sci., vol. 14, doi:10.3390/ijms14046542, pp. 6542-6555, 2013.
Elberg et al., "Prostaglandin E2 stimulates cystogenesis through EP4 receptor in IMCD-3 cells", Prostaglandins and Other Lipid Mediators, vol. 98, pp. 11-16, 2012.
Filipenko et al., "Upregulation of the S1P3 receptor in metastatic breast cancer cells increases migration and invasion by induction of PGE2 and EP2/EP4 activation", Biochimica et Biophysica Acta 1861, pp. 1840-1851, 2016.
Folco et al., "Eicosanoids From Biotechnology to Therapeutic Applications", NATO ASI Series, vol. 283, pp. 1-23, 1996.
Gustafsson et al., "EP1-4 subtype, COX and PPARγ receptor expression in colorectal cancer in prediction of disease-specific mortality", Int. J. Cancer, vol. 121, pp. 232-240, 2007.
Holt et al., "Modulation of host natural killer cell functions in breast cancer via prostaglandin E2 receptors EP2 and EP4", J Immunother, vol. 35, No. 2, doi:10.1097/CJI.0b013e318247a5e9, pp. 179-188, 2012.
Hong et al., "Paricalcitol attenuates lipopolysaccharide-induced inflammation and apoptosis in proximal tubular cells through the prostaglandin E2 receptor EP4", Kidney Research and Clinical Practice, vol. 36, pp. 145-158, 2017.
Hsu et al., Prostaglandin E2-Induced COX-2 Expressions via EP2 and EP4 Signaling Pathways in Human LoVo Colon Cancer Cells, International Journal of Molecular Sciences, vol. 18, No. 1132, pp. 1-16, 2017.
Huang et al., "Significance of Divergent Expression of Prostaglandin EP4 and EP3 Receptors in Human Prostate Cancer", Molecular Cancer Research, vol. 11, No. 4, DOI: 10.1158/1541-7786.MCR-12-0464, pp. 427-439, Apr. 2013.
Ichikawa et al., "Molecular aspects of the structures and functions of the prostaglandin E receptors", J. Lipid Mediators Cell Signalling, vol. 14, pp. 83-87, 1996.
Jain et al., "Prostaglandin E2 Regulates Tumor Angiogenesis in Prostate Cancer", Cancer Research, vol. 68, No. 19, pp. 7750-7759, Oct. 1, 2008.
Jiang et al., "Small molecule antagonist reveals seizure-induced mediation of neuronal injury by prostaglandin E2 receptor subtype EP2", PNAS, vol. 109, No. 8, pp. 3149-3154, Feb. 21, 2012.
Jiang et al., "Inhibition of the prostaglandin receptor EP2 following status epilepticus reduces delayed mortality and brain inflammation", PNAS, vol. 110, No. 9, pp. 3591-3596, Feb. 26, 2013.
Jin et al., "Prostaglandin E2 receptor subtype 2 (EP2) regulates microglial activation and associated neurotoxicity induced by aggregated a-synuclein", Journal of Neuroinflammation, vol. 4, No. 2, pp. 1-10, 2007.
Kalinski, Pawel, "Regulation of Immune Responses by Prostaglandin E2", The Journal of Immunology, vol. 188, pp. 21-28, 2012.
Kashiwagi et al., "Prostaglandin receptors induce urothelial tumourigenesis as well as bladder cancer progression and cisplatin resistance presumably via modulating PTEN expression", British Journal of Cancer, vol. 118, doi: 10.1038/bjc.2017.393, pp. 213-223, 2018.
Kobayashi et al., "Function of prostanoid receptors: studies on knockout mice", Prostaglandins & other Lipid Mediators, vol. 68-69, pp. 557-573, 2002.
Li et al., "The EP4 antagonist, L-161,982, induces apoptosis, cell cycle arrest and inhibits prostaglandin E2 induced proliferation in oral squamous carcinoma Tca8113 cells", J Oral Pathol Med., vol. 46, No. 10, pp. 1-15, Nov. 2017.
Li et al., "PGE2 promotes renal carcinoma cell invasion through activated RalA", Oncogene, vol. 32, pp. 1408-1415, 2013.
Liang et al., "The PGE2 EP2 receptor accelerates disease progression and inflammation in a model of amyotrophic lateral sclerosis", Ann Neurol., vol. 64, No. 3, doi:10.1002/ana.21437, pp. 304-314, Sep. 2008.
Liang et al., "Deletion of the Prostaglandin E2 EP2 Receptor Reduces Oxidative Damage and Amyloid Burden in a Model of Alzheimer's Disease", J. Neurosci, vol. 25, No. 44, pp. 10180-10187, Nov. 2, 2005.
Lin et al., "PGE2/EP4 antagonism enhances tumor chemosensitivity by inducing extracellular vesicle-mediated clearance of cancer stem cells", International Journal of Cancer, vol. 143, pp. 1440-1455, 2018.

(56) References Cited

OTHER PUBLICATIONS

Liu et al., "Prostaglandin E2 mediates proliferation and chloride secretion in ADPKD cystic renal epithelia", Am J Physiol Renal Physiol, vol. 303, pp. F1425-F1434, 2012.

Majumder et al., "EP4 as a Therapeutic Target for Aggressive Human Breast Cancer", International Journal of Molecular Sciences, vol. 19, No. 1019, pp. 1-20, 2018.

Murase et al., "Effect of prostanoid EP4 receptor antagonist, CJ-042,794, in rat models of pain and inflammation", European Journal of Pharmacology, vol. 580, pp. 116-121, 2008.

Murase et al., "In vitro pharmacological characterization of CJ-042794, a novel, potent, and selective prostaglandin EP4 receptor antagonist", Life Sciences, vol. 82, pp. 226-232, 2008.

Mutoh et al., "Involvement of Prostaglandin E Receptor Subtype EP4 in Colon Carcinogenesis1", Cancer Research, vol. 62, pp. 28-32, Jan. 1, 2002.

Narendra et al., "Immune system: a double-edged sword in cancer", Inflammation Research, vol. 62, pp. 823-834, 2013.

O'Callaghan et al., "Prostaglandin E2 and the EP receptors in malignancy: possible therapeutic targets?", British Journal of Pharmacology, vol. 172, pp. 5239-5250, 2015.

Okumura et al., "Discovery of AAT-008, a novel, potent, and selective prostaglandin EP4 receptor antagonist", Bioorganic & Medicinal Chemistry Letters, vol. 27, pp. 1186-1192, 2017.

Park et al., "Prostaglandin E2 Secreted by Thyroid Cancer Cells Contributes to Immune Escape Through the Suppression of Natural Killer (NK) Cell Cytotoxicity and NK Cell Differentiation", Frontiers in Immunology, vol. 9, Article 1859, pp. 1-13, Aug. 2018.

Sugimoto et al., "Prostaglandin E Receptors", The Journal of Biological Chemistry, vol. 282, No. 16, pp. 11613-11617, Apr. 20, 2007.

Thieme et al, "EP4 inhibition attenuates the development of diabetic and non-diabetic experimental kidney disease", Scientific Reports, vol. 7, No. 3442, pp. 1-11, 2017.

Tian et al., "PGE2 receptor EP2 mediates the antagonistic effect of COX-2 on TGF-β signaling during mammary tumorigenesis", The FASEB Journal, vol. 24, pp. 1105-1116, Apr. 2010.

Vaid et al., "Therapeutic intervention of proanthocyanidins on the migration capacity of melanoma cells is mediated through PGE2 receptors and β-catenin signaling molecules", Am J Cancer Res., vol. 5, No. 11, pp. 3325-3338, 2015.

Wang et al., "Elimination of CD4lowHLA-G+ T cells overcomes castration-resistance in prostate cancer therapy", Cell Research, vol. 28, pp. 1103-1117, 2018.

Wang et al., "Activation of PGE2/EP2 and PGE2/EP4 signaling pathways positively regulate the level of PD-1 in infiltrating CD8+ T cells in patients with lung cancer", Oncology Letters, vol. 15, pp. 552-558, 2018.

Woodward et al., "International Union of Basic and Clinical Pharmacology. LXXXIII: Classification of Prostanoid Receptors, Updating 15 Years of Progress", Pharmacological Reviews, vol. 63, pp. 471-538, 2011.

N-BENZYL-2-PHENOXYBENZAMIDE DERIVATIVES AS PROSTAGLANDIN E2 (PGE2) RECEPTORS MODULATORS

CROSS REFERENCE TO RELATED APPLICATIONS

This is a U.S. National Phase application claiming priority to PCT/EP2020/053069, filed Feb. 7, 2020, which claims priority to European application No. 19382088.3, filed Feb. 8, 2019, the entire contents of which are hereby incorporated by reference in their entirety.

FIELD OF THE INVENTION

The present invention relates to novel, optionally substituted, N-benzyl-2-phenoxybenzamide derivatives as modulators of the EP4 and/or EP2 receptors of prostaglandin E2 (PGE2).

Other objectives of the present invention are to provide a procedure for preparing these compounds; pharmaceutical compositions comprising an effective amount of these compounds and said compounds for use in the treatment of pathological conditions or diseases that can improve by modulators of the EP4 and/or EP2 receptors, such as cancer disease, pain and inflammation condition such as acute and chronic pain, osteoarthritis, rheumatoid arthritis diseases, endometriosis and kidney diseases.

STATE OF THE ART

Prostaglandin E2 (PGE2) is involved in several biological processes such as pain, fever, regulation of vascular tone, renal function, mucosal integrity, inflammation, angiogenesis and tumor growth. PGE2 often causes complex and divergent effects which can be attributed to its activation of four so-called E-type prostanoid receptors (EP1 to EP4). The physiological activities of PGE2 are mediated by 4 G-protein-coupled plasma membrane receptors identified as E prostanoid receptors 1-4 (EP1, EP2, EP3 and EP4), which can each activate different downstream signalling pathways. (SUGIMOTO, Yukihiko; NARUMIYA, Shuh. *Prostaglandin E receptors. Journal of Biological Chemistry*, 2007, vol. 282, no 16, p. 11613-11617).

PGE2 is a predominant eicosanoid detected in inflammation conditions, and in addition, it is also involved in various physiological and/or pathological conditions such as hyperalgesia, uterine contraction, digestive peristalsis, awakeness, suppression of gastric acid secretion, blood pressure, platelet function, bone metabolism, angiogenesis, cancer metastasis, and the like. Eicosanoids: (*From Biotechnology to Therapeutic Applications*, Folco, Samuelsson, Maclouf and Velo eds, Plenum Press, New York, 1996, chapter 14, p. 137-154); (*Journal of Lipid Mediators and Cell Signalling*, 14: 83-87 (1996)), (*Prostaglandins and Other Lipid Mediators*, 69: 557-573 (2002)).

On the other hand, it is reported that PGE2 is highly expressed in the cancer tissue in the different types of cancer, and it is also clarified that PGE2 relates to the development of cancer and disease condition. It is known that PGE2 relates to activation of cell proliferation and inhibition of cell death (apoptosis) and plays an important role in the process of cancer progression and metastasis.

Each EP receptor subtype is specifically distributed in the human body; EP1: myometrium, pulmonary veins, colon, skin, mast cells; EP2: leukocytes, smooth muscle, central nervous system (CNS), reproductive system, bones; EP3: CNS, cardiovascular system, reproductive system, kidney, urinary bladder; EP4: leukocytes, smooth muscle, cardiovascular system and bones (SUGIMOTO, Yukihiko; NARUMIYA, Shuh. *Journal of Biological Chemistry*, 2007, vol. 282, no 16, p. 11613-11617), and (Woodward, D. F. et al. (2011) *International Union of Basic and Clinical Pharmacology. LXXXIII: Pharmacol. Rev.* 63, 471-538 5).

EP2 Receptor

Studies using EP2 receptor knockout mice have demonstrated a role for the EP2 receptor in malignancy, with EP2 receptor deficient mice developing significantly less lung, skin and breast tumours following exposure to carcinogenic promoters. Genetic ablation of the EP2 receptor also decreased both the size and number of intestinal polyps in adenomatous polyposis coli (APC) 1309 mice, which are genetically susceptible to intestinal polyp development. Moreover, the EP2 receptor has been shown to be expressed by tumour cells in several cancers, including colon, prostate and breast cancer (GUSTAFSSON, Annika, et al. *International journal of cancer*, 2007, vol. 121, no 2, p. 232-240) and (Chang S H, et al. (2004). *Proc Natl Acad Sci USA* 101: 591-596).

In prostate cancer, it is known that Androgen deprivation therapy (ADT) is a main treatment but the disease often recurs and becomes castration-resistant in nearly all patients. Mechanistically, it was identified that following androgen deprivation, elevated PGE2-EP2 signaling inhibited the expression of CD4 in thymocytes. Therapeutically, inactivating PGE2 signaling with celecoxib, dramatically suppressed the onset of castration-resistant prostate cancer (CRPC). These results indicate a new therapeutic avenue of combining ADT with PGE2 inhibition for the treatment of prostate cancer (WANG, C., et al. Cell research, 2018).

PGE2-EP2 signaling functions as a node of chronic inflammation which shapes the tumor microenvironment and thus is a strong candidate of target for the chemoprevention of colorectal cancer (AOKI, Tomohiro; NARUMIYA, Shuh. *Inflammation and regeneration*, 2017, vol. 37, no 1, p. 4.)

In addition, a recent study showed that EP2 receptor activation by PGE2 markedly enhanced hepatocellular carcinoma cell invasion and migration ability by upregulating the expression level of Snail, a key inducer of EMT (CHENG, Shan-Yu, et al. *Oncology reports*, 2014, vol. 31, no 5, p. 2099-2106.) and (ZANG, Shengbing, et al. *Human pathology*, 2017, vol. 63, p. 120-127). The EP2 receptor has also been linked to metastasis in breast cancer, in part through its ability to alter the response of cells to TGF-β (Tian M, Schiemann W P (2010). FASEB J 24: 1105-1116).

EP2 Antagonism for Neurodegenerative Diseases

Chronic inflammatory neurodegenerative diseases such as epilepsy, Alzheimer disease (AD), Parkinson disease (PD) and amyotrophic lateral sclerosis (ALS) contribute to the mortality and morbidity of a significant fraction of the population. AD and PD are particularly associated with dementia symptoms in the elderly. However, all of these diseases share a common feature of overactivated inflammatory pathways. Interestingly, PGE2 is a major prostaglandin produced during the progression of these diseases and has been shown to mediate proinflammatory functions via EP2 (and to a lesser extent by EP4) receptors. Studies have shown that administration of a potent and selective EP2 antagonist, TG4-15585, substantially blocks neuronal damage in the hippocampus (>60% in the hilus, 80% in the CA3 and >90% in the CA1 region) in a pilocarpine model of status epilepticus. (JIANG, Jianxiong, et al. *Proceedings of the National Academy of Sciences,* 2012, vol. 109, no 8, p. 3149-3154).

Another potent EP2 antagonist, TG6-10-186, suppresses neurodegeneration, upregulation of inflammatory cytokines and chemokines and activation of glia in mice following status epilepticus, suggesting a potential therapeutic benefit for an EP2 antagonist to block epileptogenesis. (JIANG, Jianxiong, et al. *Proceedings of the National Academy of Sciences,* 2013, vol. 110, no 9, p. 3591-3596).

Based on beneficial effects observed in EP2-knockout mouse models of AD, PD and ALS (vide supra), an EP2 receptor antagonist may show utility as an adjunct therapeutic agent for chronic inflammatory neurodegenerative diseases including epilepsy, alzheimer disease, Parkinson disease, and amyotrophic lateral sclerosis. (LIANG, Xibin, et al. *Annals of Neurology: Official Journal of the American Neurological Association and the Child Neurology Society,* 2008, vol. 64, no 3, p. 304-314). (Liang X, et al. *J. Neurosci.* 2005; 25:10180-10187); (Jin J, et al. *Journal of Neuroinflammation.* 2007).

EP4 Receptor

The EP4 receptor, unlike the EP2 receptor, is expressed in a variety of tissues and cells, including the immune, osteoarticular, cardiovascular, gastrointestinal, and respiratory systems, and cancer cells. Recent findings have suggested that the regulation of EP4 signaling could be involved in therapeutic strategies for colon cancer (MUTOH, Michihiro, et al. *Cancer research,* 2002, vol. 62, no 1, p. 28-32.), aortic aneurysm (YOKOYAMA, Utako, et al. *PloS one,* 2012, vol. 7, no 5, p. e36724.), rheumatoid arthritis (CHEN, Q., et al. *British journal of pharmacology,* 2010, vol. 160, no 2, p. 292-310.), osteoporosis and autoimmune disease (YAO, Chengcan, et al. *Nature medicine,* 2009, vol. 15, no 6, p. 633.).

Accordingly, the regulation of EP4 signaling has received even greater attention as a potential therapeutic target.

Recent reports suggest that the EP4 receptor which is expressed in certain types of cancer promotes tumor cell proliferation and metastasis (YOKOYAMA, et al. *Pharmacological reviews,* 2013, vol. 65, no 3, p. 1010-1052).

In breast cancer, studies have demonstrated that tumor progression and metastasis due to multiple cellular events, including inactivation of host anti-tumor immune cells, such as Natural Killer (NK) and T cells, increased immunosuppressor function of tumor-associated macrophages, promotion of tumor cell migration, invasiveness and tumor-associated angiogenesis, due to upregulation of multiple angiogenic factors including Vascular Endothelial Growth Factor (VEGF)-A, increased lymphangiogenesis (due to upregulation of VEGF-C/D), and a stimulation of stem-like cell (SLC) phenotype in cancer cells, were primarily mediated by activation of the Prostaglandin (PG) E receptor EP4 on tumor or host cells, and that selective EP4 antagonists could mitigate all of these events tested with cells in vitro as well as in vivo in syngeneic COX-2 expressing mammary cancer bearing mice or immune-deficient mice bearing COX-2 over-expressing human breast cancer xenografts. (MAJUMDER, Mousumi, et al. *International journal of molecular sciences,* 2018, vol. 19, no 4, p. 1019).

EP4 expression levels were also correlated with prostate cancer cell invasiveness and EP4 specific antagonist ONO-AE3-208 suppressed cell invasion, migration, and bone metastasis (XU, Song, et al. *Cell biochemistry and biophysics,* 2014, vol. 70, no 1, p. 521-527).

Other study has demonstrated that inhibition of EP4 attenuates the renal cell carcinoma (RCC) intravasation and metastasis by downregulating CD24 and that P-selectin participates in tumor intravasation, implying a potential for these molecules as therapeutic targets for advanced RCC treatment. (ZHANG, Yushan, et al. *Cancer letters,* 2017, vol. 391, p. 50-58).

EP4 antagonist, L-161,982, induces apoptosis, cell cycle arrest and inhibits prostaglandin E2 induced proliferation in oral squamous carcinoma Tca8113 cells. (LI, Xiaohui, et al. *The Journal of Oral Pathology & Medicine,* 2017, vol. 46, no 10, p. 991-997).

Other study demonstrated that EP4 antagonism, a more selective inhibition of PGE2 signaling, reduces the number of cancer stem cells (CSCs) in tumors and increases chemosensitivity of tumors. EP4 antagonism converts CSCs to chemotherapy-sensitive non-stem cells by triggering extracellular vesicle/exosome release, and enhances tumor responses to conventional chemotherapy. (LIN, Meng-Chieh, et al. *International journal* of cancer, 2018).

In addition, selective EP4 receptor antagonists are also expected to offer an attractive therapeutic approach for autoimmune diseases such as inflammatory bowel disease (IBD), rheumatoid arthritis (RA), and multiple sclerosis (MS)16-18 through the inhibition of interleukin-23 (IL-23) production and suppression of T helper 1 (Th1) and T helper 17 (Th17).

The role of the EP4 receptor in liver cancer has recently been reported in non-patent literatures. PGE2/EP4 receptor signaling through PKA/CREB activation upregulated c-Myc expression and resulted in promoting cell growth in HCC cells in vitro (XIA, Shukai, et al. *Oncology reports,* 2014, vol. 32, no 4, p. 1521-1530).

PGE2-activated EP4 receptor signalling may be involved in various pathologic states, such as pain (in particular inflammatory, neuropathic and visceral), inflammation, neuroprotection, dermatitis, bone disease, immune system dysfunction promotion of sleep, renal regulation, gastric or enteric mucus secretion and duodenal bicarbonate secretion. Studies suggest that PGE2 inhibits proteoglycan synthesis and stimulates matrix degradation in osteoarthritic chondrocytes via the EP4 receptor. Targeting EP4, rather than cyclooxygenase 2, could represent a future strategy for osteoarthritis disease modification. (ATTUR, Mukundan, et al. *The Journal of Immunology,* 2008, vol. 181, no 7, p. 5082-5088). Other study suggests that a pharmacological blockade of the prostanoid EP4 receptor may represent a new therapeutic strategy in signs and symptomatic relief of osteoarthritis and/or rheumatoid arthritis. (MURASE, Akio, et al. *European journal of pharmacology,* 2008, vol. 580, no 1-2, p. 116-121).

On the other hand, some studies have shown the implication of EP4 receptor in the development of kidney diseases.

In this sense, recent study has demonstrated the renoprotective properties of PGE2 EP4 receptor-selective antagonist ASP7657 in 5/6 nephrectomized rats, a chronic kidney disease (CKD) model. This study suggests that ASP7657 suppresses the progression of chronic renal failure by modulating renin release and improving renal hemodynamics (ELBERG, Dorit, et al. *Prostaglandins & other lipid mediators,* 2012, vol. 98, no 1-2, p. 11-16).

Other study discloses EP4 antagonism improves the nephrotoxic serum nephritis NTS phenotype probably by decreasing mainly Cxcl-5 production in tubular cells thereby reducing renal neutrophil infiltration (ARINGER, Ida, et al. *American Journal of Physiology—Renal Physiology,* 2018).

In rodent models of diabetic and non-diabetic chronic kidney disease (CKD), EP4 inhibition attenuated renal injury through mechanisms that were distinct from either broadspectrum COX inhibition or "standard of care" renin angiotensin system blockade. (THIEME, Karina, et al. *Scientific Reports*, 2017, vol. 7, no 1, p. 3442.)

Finally, other study mentions EP4 plays a pivotal role in anti-inflammatory and antiapoptotic effects through Akt and NF-κB signaling after paricalcitol pretreatment in lipopolysaccharide (LPS)-induced renal proximal tubule cell injury. (HONG, Yu Ah, et al. *Kidney research and clinical practice*, 2017, vol. 36, no 2, p. 145).

It is known that Prostaglandin E2 (PGE2) contributes to cystogenesis in genetically nonorthologous models of autosomal dominant polycystic kidney disease (ADPKD). PGE2 activates aberrant signaling pathways in renal epithelial cells deficient in polycystin-1 (PC-1) that contribute to the proliferative and secretory phenotype characteristic of ADPKD. Antagonizing EP4 receptors reverted the growth advantage of renal epithelial cells deficient in polycystin-1 (PC-1-deficient cells), implicating a central role for the EP4 receptor in proliferation. (LIU, Yu, et al. *American Journal of Physiology—Renal Physiology*, 2012, vol. 303, no 10, p. F1425-F1434).

Prostaglandin E2 (PGE2) stimulates cAMP formation and cyst formation in human ADPKD cells. Studies performed in isolated human ADPKD renal epithelial cells, shown that effect of PGE2 appears to be mediated by EP2 receptors, suggesting the therapeutic potential of EP2 receptor antagonists in the treatment of cystogenesis in ADPKD. Prostanoid-E receptor selective antagonists that inhibit EP2 or EP4 receptor activities may be used as a pharmacological strategy to limit cyst formation and ADPKD progression. (ELBERG, Dorit, et al. *Prostaglandins & other lipid mediators*, 2012, vol. 98, no 1-2, p. 11-16).

EP2 and EP4 receptors modulation are also implicated in several diseases.

Activation of PGE2/EP2 and PGE2/EP4 signaling pathways positively regulate the level of PD-1 in infiltrating CD8+ T cells in patients with lung cancer which results in immune tolerance in the lung cancer microenvironment. (WANG, Jinhong, et al. Oncology letters, 2018, vol. 15, no 1, p. 552-558).

EP2/EP4 activation correlates with induction of urothelial cancer initiation and outgrowth, as well as chemoresistance, presumably via downregulating phosphatase and tensin homologue (PTEN) expression. In BC lines, EP2/EP4 antagonists and celecoxib effectively inhibited cell viability and migration, as well as augmented PTEN expression (KASHIWAGI, Eiji, et al. *British journal of cancer*, 2018, vol. 118, no 2, p. 213.)

It is known that upregulation of the S1P3 receptor in metastatic breast cancer cells increases migration and invasion by induction of PGE2 and EP2/EP4 activation. (FILIPENKO, Iuliia, et al. *Biochimica et biophysica acta (BBA)-molecular and cell biology of lipids*, 2016, vol. 1861, no 11, p. 1840-1851).

It is also known that human prostate cancer is associated with EP4 and EP2 overexpression and reduced EP3 expression (HUANG, Hosea F S, et al. *Significance of divergent expression of prostaglandin EP4 and EP3 receptors in human prostate cancer. Molecular Cancer Research*, 2013, p. molcanres. 0464.2012). Likewise, other study showed that prostaglandin E2 regulates tumor angiogenesis in prostate cancer through E prostanoid 2 (EP2)-mediated and EP4-mediated pathways. (JAIN, Shalini, et al. *Cancer Research*, 2008, vol. 68, no 19, p. 7750-7759).

Other studies mention that PGE2 increases SN12C cell invasion through a signal pathway that encompasses EP2 and EP4, promoting renal carcinoma cell invasion. (LI, Zhenyu, et al. *PGE2 promotes renal carcinoma cell invasion through activated RalA. Oncogene*, 2013, vol. 32, no 11, p. 1408) and (LI, Zhenyu, et al. *Oncogene*, 2013, vol. 32, no 11, p. 1408).

PGE2 receptors (EP2 and EP4) agonists promote melanoma cell migration while PGE2 receptor antagonist suppressed the migration capacity of melanoma cells, a highly aggressive form of skin cancer. (VAID, Mudit, et al. *American journal of cancer research*, 2015, vol. 5, no 11, p. 3325).

In addition, it has been evidenced that Inhibition of EP2 and EP4 shows that PGE2 induces protein expression of COX-2 through EP2 and EP4 receptors in LoVo colon cancer cells. (HSU, Hsi-Hsien, et al. *International journal of molecular sciences*, 2017, vol. 18, no 6, p. 1132).

Others studies have demonstrated that inhibition of EP2/EP4 decreases growth and survival of endometriosis lesions; decreases angiogenesis and innervation of endometriosis lesions; suppresses proinflammatory state of dorsal root ganglia neurons to decrease pelvic pain; decreases proinflammatory, estrogen-dominant, and progesterone-resistant molecular environment of the endometrium and endometriosis lesions; and restores endometrial functional receptivity through multiple mechanisms (AROSH, Joe A., et al. *Proceedings of the National Academy of Sciences*, 2015, vol. 112, no 31, p. 9716-9721) (Banu, S. K.; Lee, J.; Speights, V. O., Jr.; Starzinski-Powitz, A.; Arosh, J. A. *Molecular Endocrinology* 2009, 23, 1291-1305) and new selective EP4 antagonists have been identified for the treatment of endometriosis (BÄURLE, Stefan, et al. *Identification of a Benzimidazolecarboxylic Acid Derivative (BAY 1316957) as a Potent and Selective Human Prostaglandin E2 Receptor Subtype 4 (hEP4-R) Antagonist for the Treatment of Endometriosis. Journal of Medicinal Chemistry*, 2019).

EP2 and EP4 in Immune Response

In tumors of different entities, all four receptors are relevant, but expression of EP2 and EP4 receptors is much more dominant on immune cells rather than tissue-resident cells.

PGE2-induced EP2 receptor signalling also plays an important role in suppressing the antitumour immune response. Indeed, most of the immunomodulatory effects of PGE2 on immune cells occur as a result of signalling through the EP2 and EP4 receptors (KALINSKI, Pawel. *The Journal of Immunology*, 2012, vol. 188, no 1, p. 21-28.). This is probably due to the fact that signalling through both these receptors is transduced by the same Gas stimulatory protein, and upon activation leads to an increase in the intracellular concentration of cAMP. This increase in cAMP was shown to be responsible for the inhibition of T helper (TH)1 cells and the associated reduction in IL-2 and IFNγ, which is important given that CD4+TH cells represent a key effector arm of the adaptive immune system required for cancer control. (O'CALLAGHAN, G.; HOUSTON, A. *British journal of pharmacology*, 2015, vol. 172, no 22, p. 52).

PGE2 also inhibits, in an EP2 and EP4 receptor-mediated fashion, the activity of NK cells and cytotoxic T cells (CTL) (HOLT, Dawn, et al. *Journal of immunotherapy*, 2012, vol. 35, no 2, p. 179.) two cell types that can also form part of the antitumour immune response. In addition, to directly suppressing the activity of immune cells, signalling through the EP2 and EP4 receptors promotes the development of Treg cells. Treg cells are potent inhibitors of the immune system, suppressing the activity of numerous immune cells, including dendritic cells (DCs) (NARENDRA, Bodduluru Lakshmi, et al. *Inflammation Research*, 2013, vol. 62, no 9, p. 823-834.). DCs play a central role in the initiation of the tumour-specific immune response, with the presence of DCs in tumours correlating with improved prognosis. Signalling through the EP2 (and EP4) receptors not only blocked the activity of DCs through the induction of Treg cells but also blocked their generation from monocytes, resulting instead in the development of the immunosuppressive MDSCs from monocytes (DE KEIJZER, Sandra, et al. *International journal of molecular sciences*, 2013, vol. 14, no 4, p. 6542-6555.).

Activation of PGE2/EP2 and PGE2/EP4 signaling pathways positively regulate the level of PD-1 in infiltrating CD8+ T cells in patients with lung cancer. (WANG, Jinhong, et al. *Oncology letters*, 2018, vol. 15, no 1, p. 552-558).

Other study demonstrated that PGE2 produced by thyroid cancer cells suppressed the cytolytic activity of NK cells by inhibiting the expression of NK activating receptors through EP2 and EP4 receptors on NK cells. (PARK, Arum, et al. *Frontiers in immunology*, 2018, vol. 9).

On the other hand, it have been shown that a specific EP4 blockade by E7046 a EP4 antagonist reversed the PGE2-induced myeloid-mediated immunosuppression and that E7046 in combination with E7777 an IL-2-diphtheria toxin fusion protein that preferentially kills Tregs, synergistically mitigated both myeloid and Treg-derived immunosuppression within the TME, to promote robust anti-tumor immune responses, providing a combination therapy which may benefit cancer patients with tumors enriched in myeloid and Treg cells (ALBU, Diana I., et al. *Oncoimmunology*, 2017, vol. 6, no 8, p. e1338239).

Hence, the problem to be solved by the present invention is to provide compounds as modulators of EP4 and/or EP2 receptors of prostaglandin E2 (PGE2).

The authors of the present invention have discovered new N-benzyl-2-phenoxybenzamide derivatives conveniently substituted as potent modulators of EP4 and/or EP2 receptors of PGE2. The compounds would therefore be useful for the treatment diseases or conditions mediated by modulation of EP4 and/or EP2 receptors, such as cancer, pain such as acute and chronic pain, inflammation such as osteoarthritis, rheumatoid arthritis, neurodegenerative diseases, endometriosis and kidney diseases.

SUMMARY OF THE INVENTION

In a first aspect (aspect 1), the present invention refers to new N-benzyl-2-phenoxybenzamide derivatives of formula (I):

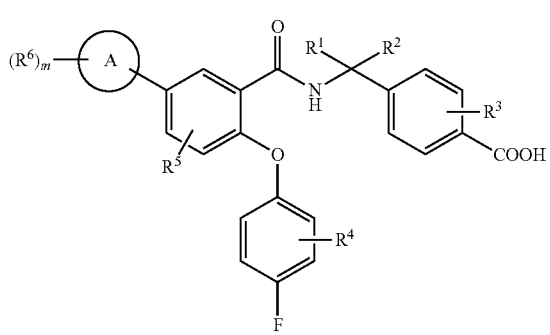

wherein:
A represents a group selected from phenyl and five or six-membered heteroaryl with one, two or three heteroatoms selected from N, S and O,
$R^1$ and $R^2$ represent independently a group selected from hydrogen atom, halogen atom and $C_{1-3}$ alkyl, or $R^1$ and $R^2$ together with the carbon atom to which they are attached form a $C_{3-4}$ cycloalkyl group,
$R^3$, $R^4$, $R^5$ and each $R^6$ represent independently a group selected from hydrogen atom, halogen atom, cyano group, linear or branched $C_{1-3}$ haloalkyl group, linear or branched $C_{1-3}$ alkyl, $C_{3-4}$ cycloalkyl, linear or branched $C_{1-3}$ alkoxy and a pyridyl group,
m is and integer from 1 to 5,
and pharmaceutically acceptable salts thereof.

Other aspects of the present invention are:
Aspect 2) processes for the preparation of the compounds of aspect 1.
Aspect 3) pharmaceutical compositions comprising a therapeutically effective amount of a compound of aspect 1.
Aspect 4) pharmaceutical compositions according to aspect 3 further comprising a therapeutically effective amount of chemotherapeutics agents, anti-inflammatory agents, steroids, immunotherapeutic agent and other agents such as therapeutic antibodies.
Aspect 5) Compounds of aspect 1 for use in the treatment of diseases that can be ameliorated by modulation of EP4 and/or EP2 receptors of prostaglandin E2 (PGE2).
Diseases that may be ameliorated by modulation of EP4 and/or EP2 receptors may be selected from the group consisting of cancer, pain, inflammation, neurodegenerative diseases and kidney diseases. Cancer is preferably selected from colon cancer, gastric cancer, prostate cancer, lung cancer, hepatocellular carcinoma, renal carcinoma and breast cancer.
Aspect 6) Use of the compounds of aspect 1 or the pharmaceutical compositions of aspect 3 or 4 in the manufacture of a medicament for the treatment of diseases that can be ameliorated by modulation of EP4 and/or EP2 receptors.
Aspect 7) Methods for the treatment or prevention of diseases that can be ameliorated by modulation of EP4 and/or EP2 receptors by administration of the compounds of aspect 1 or the pharmaceutical compositions of aspect 3 or 4 to a subject in need of said treatment.
Aspect 8) combination products comprising a compound of formula (I) or a pharmaceutically acceptable salt thereof and one or more therapeutic agents selected from the group consisting of chemotherapeutics agents, anti-inflammatory agents, steroids, immunosuppressants, therapeutic antibodies, that can be used in combination with the compounds of the present application for treatment of diseases, disorders or conditions associated with the modulation of receptors EP4 and/or EP2 of prostaglandin E2. The one or more additional pharmaceutical agents can be administered to a patient simultaneously or sequentially.

Example chemotherapeutics agents include proteosome inhibitors (e.g., bortezomib), chemotherapeutics agents for treatment of CNS cancer including temozolomide, carboplatin, carmustine (BCNU), cisplatin, cyclophosphamide, etoposide, irinotecan, lomustine (CCNU), methotrexate, procarbazine, vincristine, and other chemotherapeutics agents such as thalidomide, revlimid, and DNA-damaging agents such as melphalan, doxorubicin, cyclophosphamide, vincristine, etoposide, carmustine, and the like.

Example anti-inflammatory compounds include aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, valdecoxib, and the like.

Example steroids include corticosteroids such as cortisone, dexamethasone, hydrocortisone, methylprednisolone, prednisolone, prednisone, and the like.

Example immunosuppressants include azathioprine, chlorambucil, cyclophosphamide, cyclosporine, daclizumab, infliximab, methotrexate, tacrolimus, and the like.

Example of therapeutic antibodies for use in combination therapy include but are not limited to trastuzumab (e.g. anti-HER2), ranibizumab (e.g. anti-VEGF-A), bevacizumab (e.g. anti-VEGF), panitumumab (e.g. anti-EGFR), cetuximab (e.g. anti-EGFR), rituxan (anti-CD20) and antibodies directed to c-MET.

In still another aspect the present invention relates to a combination product comprising compound of formula (I) or a pharmaceutically acceptable salt thereof and one or more immunotherapeutic agent useful in the treatment of cancer, selected from colon cancer, gastric cancer, prostate cancer, lung cancer, and breast cancer.

In a preferred embodiment, a combination product comprises a compound of formula (I) or a pharmaceutically acceptable salt thereof, and one or more immunotherapeutic agent selected from the group consisting of antibodies anti-CTLA4, selected from Ipilimumab and tremelimumab, antibodies anti-PD1 such as nivolumab, pembrolizumab, cemiplimab, pidilizumab, spartalizumab, MEDI0680, REGN2810 and AMP-224, antibodies anti-PDL1 such as Atezolizumab, Avelumab, Durvalumab, and MDX-1105 and monoclonal antibody that targets glycolipid GD2 as Dinutuximab. The components of the combination product are in the same formulation or in separate formulations.

Accordingly, the derivatives of the present invention and pharmaceutically acceptable salts and pharmaceutical compositions comprising such compounds and/or salts thereof, may be used in a method of treatment of pathological conditions or disease of human body which comprises administering to a subject in need of said treatment, an effective amount of the N-benzyl-2-phenoxybenzamide derivatives of the invention or a pharmaceutically acceptable salt thereof.

As it is said before, the N-benzyl-2-phenoxybenzamide derivatives of the present invention are useful in the treatment or prevention of diseases known to be susceptible to amelioration by treatment with modulators of EP4 and/or EP2 receptors of prostaglandin E2. Such diseases are selected from the group consisting of cancer such as gastric cancer, colorectal cancer, prostate cancer, lung cancer, hepatocellular carcinoma, renal carcinoma and breast cancer, pain, inflammation, neurodegenerative diseases and kidney diseases.

As used herein, the term halogen atom comprises chlorine, fluorine, bromine or iodine atom, preferably fluorine, chlorine or bromine atom, more preferably fluorine or chlorine atom. The term halo when used as a prefix has the same meaning.

As used herein, the term $C_{1-3}$ haloalkyl is used to designate $C_{1-3}$ alkyl substituted by one or more halogen atoms, preferably one, two or three halogen atoms. Preferably, the halogen atoms are selected from the group consisting of fluorine or chlorine atoms, more preferably fluorine atoms. In a preferred embodiment, the haloalkyl groups is $C_1$ alkyl substituted by three fluorine atoms (trifluoromethyl group).

As used herein the term $C_{1-3}$ alkyl is used to designate linear or branched hydrocarbon radicals ($C_nH_{2n+1}$) having 1 to 3 carbon atoms. Examples include methyl, ethyl, n-propyl, i-propyl radicals.

As used herein, the term $C_n$-$C_m$ cycloalkyl embraces hydrocarbon monocyclic groups having n to m carbon atoms, for example 3 to 6 or 3 to 4 carbon atoms. Such cycloalkyl groups include, by way of example, cyclopropyl, cyclobutyl, cyclopentyl and cyclohexyl.

As used herein, the term $C_{1-3}$ alkoxy is used to designate radicals which contain a linear or branched $C_{1-3}$ alkyl group linked to an oxygen atom ($C_nH_{2n+1}$—O—). Preferred alkoxy radicals is methoxy.

As used herein the term $C_{3-4}$ cycloalkoxy is used to designate radicals containing a $C_{3-4}$ cycloalkyl groups linked to an oxygen atom.

As used herein, the terms five to six-membered heteroaryl is used to designate an heteroaromatic ring containing carbon, hydrogen and one or more, preferably one, two or three, heteroatoms selected from N, O and S as part of the ring such as furan, pyridine, pyrimidine, pyrazine, pyrrole, imidazole, pyrazole, oxazole, thiazole and thiophene, preferably furan, pyridine, pyrazine, pyrrole, imidazole, pyrazole, oxazole, thiazole and thiophene. Said groups may optionally be substituted by one or more substituents according to what has been defined in each case. The preferred radicals are optionally substituted pyridinyl, pyrimidinyl. When a heteroaryl radical carries two or more substituents, the substituents may be the same or different.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4, substituents, whereby the hydrogen atoms bound to the unsubstituted atoms, radicals, chains or cycles are replaced by chemically acceptable atoms, radicals, chains or cycles. When two or more substituents are present, each substituent may be the same or different.

As used herein, the term pharmaceutically acceptable salt is used to designate salts with a pharmaceutically acceptable base. Pharmaceutically acceptable bases include alkali metal (e.g. sodium or potassium), alkali earth metal (e.g. calcium or magnesium) hydroxides, and organic bases, for example alkyl amines, arylalkyl amines and heterocyclic amines.

The term "modulator" refers to a molecule that blocks or otherwise interferes with the particular biological activity of the receptor.

The term "Ki", as used herein, refers to concentration causing a half-maximal inhibition of control specific binding. Ki values can be estimated from $IC_{50}$, concentration of radioligand in the assay, and affinity of the radioligand for the receptor. $IC_{50}$ values can be estimated from an appropriate dose-response curve, more accurately, $IC_{50}$ values may be determined using non-linear regression analysis.

According to one embodiment of the present invention in the compounds of formula (I), $R^1$ and $R^2$ are independently selected from hydrogen atom and $C_{1-3}$ alkyl, or $R^1$ and $R^2$ together with the carbon atom to which they are attached form a $C_{3-4}$ cycloalkyl group; $R^3$ is selected form hydrogen atom and halogen atom; and $R^4$ and $R^5$ represent hydrogen atoms.

According to one embodiment of the present invention in the compounds of formula (I), $R^1$, $R^2$, $R^3$, $R^4$ and $R^5$ represent hydrogen atoms.

According to one embodiment of the present invention, in the compounds of formula (I), A is selected from the group consisting of phenyl, piridinyl, pyrazolyl, pyrimidinyl, thiophenyl and furanyl, preferably selected from the group consisting of phenyl, piridinyl, pyrazolyl, pyrimidinyl and thiophenyl; more preferably selected from the group consisting of phenyl, piridinyl, pyrimidinyl and thiophenyl; even more preferably selected from the group consisting of phenyl, piridinyl and thiophenyl.

According to one embodiment of the present invention A represents a phenyl group.

In a preferred embodiment each $R^6$ independently represents a group selected from:
a) hydrogen atom,
b) halogen atom
c) cyano group,
d) carbamoyl (—$CONH_2$) group, and
d) linear or branched $C_{1-3}$ haloalkyl group.

In a particular embodiment each $R^6$ independently represents a group selected from:
a) hydrogen atom,
b) fluorine atom,
c) chlorine atom,
c) cyano group,
d) carbamoyl (—$CONH_2$) group, and
d) trifluoromethyl group.

In a more preferred embodiment A represents a phenyl group and each $R^6$ independently represents a group selected from fluoro, trifluoromethyl and cyano group and m is and integer from 1 to 4.

According to another embodiment of the present invention A represents a five or six-membered heteroaryl ring with one or two N atoms as part of the ring. In a preferred embodiment A represents a group selected from a pyridyl or a thiophene group, each $R^6$ independently represents a group selected from fluoro, trifluoromethyl and cyano groups and m is an integer from one to four.

According to another embodiment of the present invention $R^1$, $R^2$, $R^3$, $R^4$ and $R^5$ represent hydrogen atoms, A represents a phenyl group and each $R^6$ independently represents a group selected from fluoro or trifluoromethyl groups, and m is an integer from one to five.

According to another embodiment, m is an integer from 1 to 4, preferably m is an integer from 1 to 2.

According to another embodiment, A represents a group selected from phenyl, pyridinyl, pyrimidinyl, tiophenyl, $R^1$, $R^2$, $R^3$, $R^4$, $R^5$ are hydrogen atoms, each $R^6$ represents independently a group selected from hydrogen atom, fluorine, chlorine, cyano group, trifluoromethyl and pyridyl group and m is and integer from 1 to 2.

Particular individual compounds of the present invention include:
4-((2-(4-fluorophenoxy)-5-(pyridin-4-yl)benzamido)methyl)benzoic acid
4-((4-(4-fluorophenoxy)-[1,1'-biphenyl]-3-carboxamido)methyl)benzoic acid
4-((4'-chloro-4-(4-fluorophenoxy)-[1,1'-biphenyl]-3-carboxamido)methyl)benzoic acid
4-((4'-fluoro-4-(4-fluorophenoxy)-[1,1'-biphenyl]-3-carboxamido)methyl)benzoic acid
4-((3'-fluoro-4-(4-fluorophenoxy)-[1,1'-biphenyl]-3-carboxamido)methyl)benzoic acid
4-((2'-fluoro-4-(4-fluorophenoxy)-[1,1'-biphenyl]-3-carboxamido)methyl)benzoic acid
4-((4'-cyano-4-(4-fluorophenoxy)-[1,1'-biphenyl]-3-carboxamido)methyl)benzoic acid
4-((3'-cyano-4-(4-fluorophenoxy)-[1,1'-biphenyl]-3-carboxamido)methyl)benzoic acid
4-((2-(4-fluorophenoxy)-5-(3-fluoropyridin-4-yl)benzamido)methyl)benzoic acid)
4-((2-(4-fluorophenoxy)-5-(pyridin-3-yl)benzamido)methyl)benzoic acid
4-((2-(4-fluorophenoxy)-5-(3-chloropyridin-4-yl)benzamido)methyl)benzoic acid
4-((2-(4-fluorophenoxy)-5-(pyrimidin-5-yl)benzamido)methyl)benzoic acid
4-((3',4'-difluoro-4-(4-fluorophenoxy)-[1,1'-biphenyl]-3-carboxamido)methyl)benzoic acid
4-((4-(4-fluorophenoxy)-4'-(trifluoromethyl)-[1,1'-biphenyl]-3-carboxamido)methyl)benzoic acid
4-((4-(4-fluorophenoxy)-3'-(trifluoromethyl)-[1,1'-biphenyl]-3-carboxamido)methyl)benzoic acid
4-((2-(4-fluorophenoxy)-5-(pyridin-2-yl)benzamido)methyl)benzoic acid
4-((2-(4-fluorophenoxy)-5-(pyrimidin-4-yl)benzamido)methyl)benzoic acid
4-((2-(4-fluorophenoxy)-5-(thiophen-2-yl)benzamido)methyl)benzoic acid
4-((3',5'-difluoro-4-(4-fluorophenoxy)-[1,1'-biphenyl]-3-carboxamido)methyl))benzoic acid
4-((3'-chloro-4-(4-fluorophenoxy)-[1,1'-biphenyl]-3-carboxamido)methyl)benzoic acid
4-((3'-fluoro-4-(4-fluorophenoxy)-5'-(trifluoromethyl)-[1,1'-biphenyl]-3-carboxamido)methyl)benzoic acid
4-((3'-carbamoyl-5'-chloro-4-(4-fluorophenoxy)-[1,1'-biphenyl]-3-ylcarboxamido)methyl)benzoic acid
4-((2-(4-fluorophenoxy)-5-(1H-pyrazol-4-yl)benzamido)methyl)benzoic acid
4-((2-(4-fluorophenoxy)-5-(1-methyl-1H-pyrazol-4-yl)benzamido)methyl)benzoic acid
4-((2-(4-fluorophenoxy)-5-(1-methyl-1H-pyrazol-5-yl)benzamido)methyl)benzoic acid
4-((4-(4-fluorophenoxy)-3'-(pyridin-4-yl)-[1,1'-biphenyl]-3-ylcarboxamido)methyl)benzoic acid
4-((5-(5-carbamoylfuran-2-yl)-2-(4-fluorophenoxy)benzamido)methyl)benzoic acid
3-fluoro-4-((4-(4-fluorophenoxy)-3'-(trifluoromethyl)-[1,1'-biphenyl]-3-ylcarboxamido)methyl)benzoic acid
(R)-4-(1-(4-(4-fluorophenoxy)-3'-(trifluoromethyl)-[1,1'-biphenyl]-3-carboxamido)ethyl)benzoic acid
4-(1-(4-(4-fluorophenoxy)-3'-(trifluoromethyl)-[1,1'-biphenyl]-3-carboxamido)cyclopropyl)benzoic acid
4-((3'-fluoro-5'-cyano-4-(4-fluorophenoxy)-[1,1'-biphenyl]-3-carboxamido)methyl)benzoic acid
4-((3'-chloro-5'-cyano-4-(4-fluorophenoxy)-[1,1'-biphenyl]-3-carboxamido)methyl)benzoic acid.

The compounds of the present invention can be prepared by using the procedures described below. To facilitate the description of the procedures, concrete examples have been used, but they do not restrict the scope of the present invention in any way.

Scheme 1

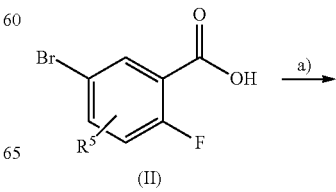

(II)

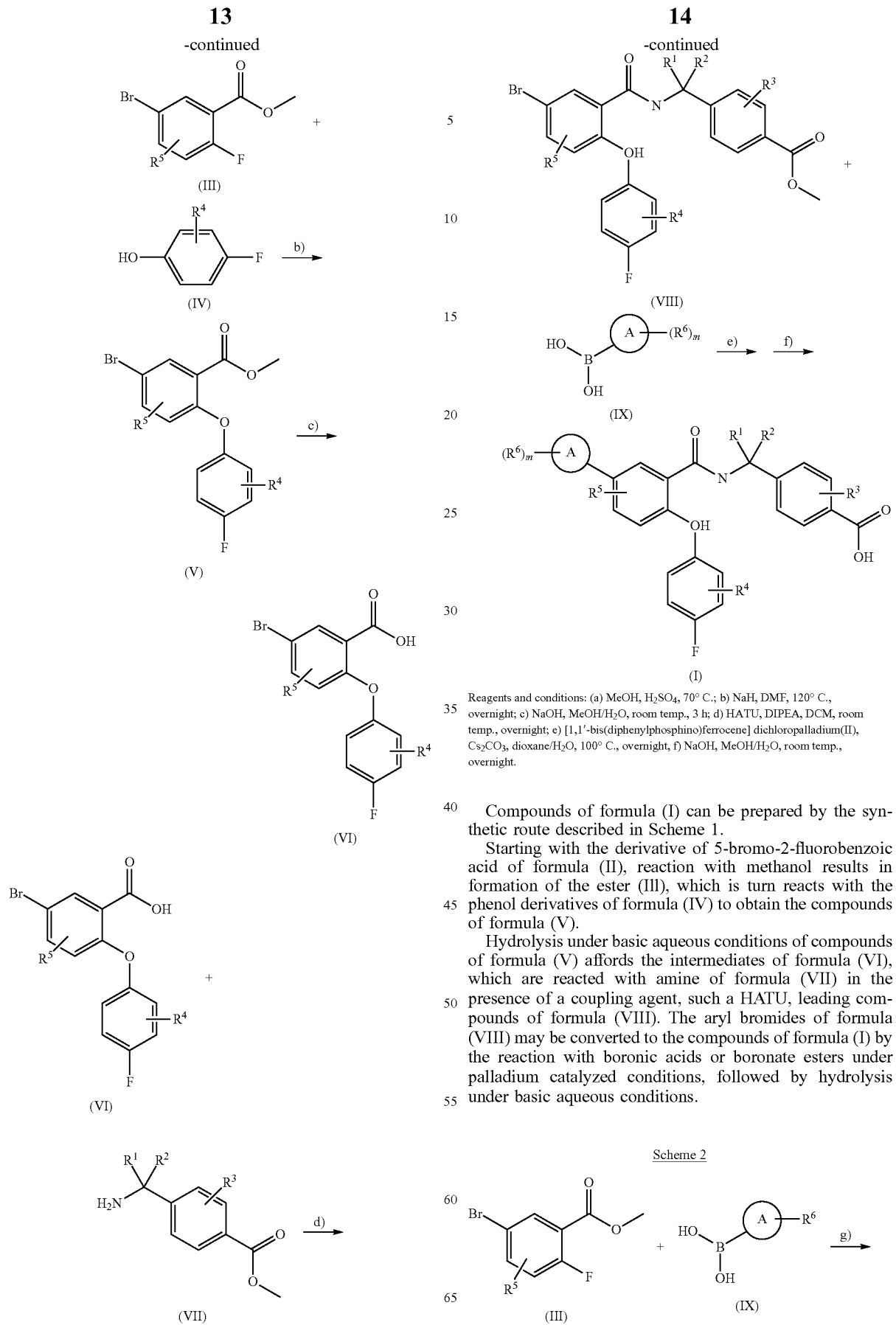

Compounds of formula (I) can be prepared by the synthetic route described in Scheme 1.

Starting with the derivative of 5-bromo-2-fluorobenzoic acid of formula (II), reaction with methanol results in formation of the ester (III), which is turn reacts with the phenol derivatives of formula (IV) to obtain the compounds of formula (V).

Hydrolysis under basic aqueous conditions of compounds of formula (V) affords the intermediates of formula (VI), which are reacted with amine of formula (VII) in the presence of a coupling agent, such a HATU, leading compounds of formula (VIII). The aryl bromides of formula (VIII) may be converted to the compounds of formula (I) by the reaction with boronic acids or boronate esters under palladium catalyzed conditions, followed by hydrolysis under basic aqueous conditions.

-continued

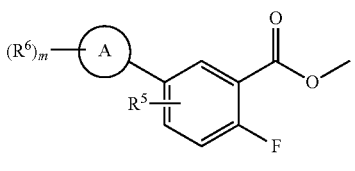

(X)

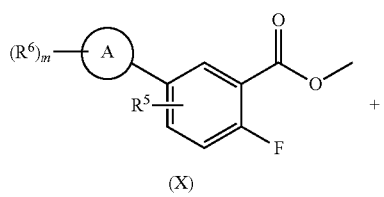

(X)

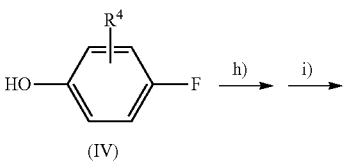

(IV)

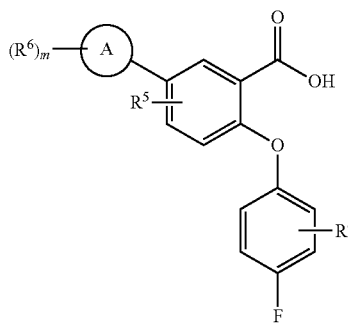

(XI)

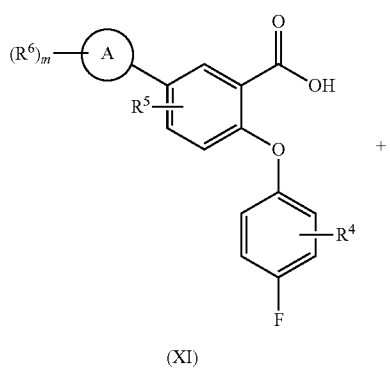

(XI)

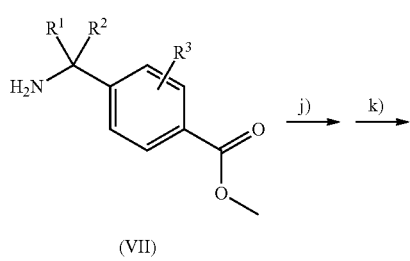

(VII)

-continued

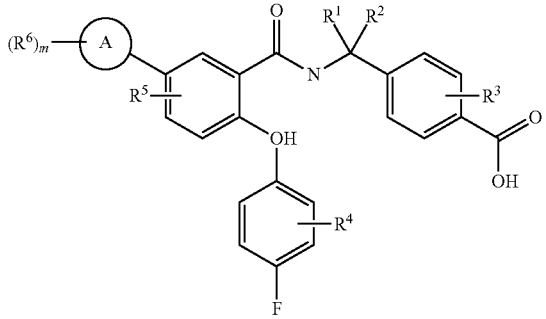

(I)

Reagents and conditions: g) [1,1'-bis(diphenylphosphino)ferrocene]dichloropalladium (II), Cs₂CO₃, dioxane/H₂O, 100° C., overnight, h) NaH, DMF, 120° C., overnight; i) NaOH, MeOH/H₂O, room temp., overnight;) HATU, DIPEA, DCM, room temp., overnight; k) NaOH, MeOH/H₂O, room temp., overnight.

An alternative route to compounds of formula (I) is depicted in Scheme 2. Aryl bromides of formula (III) react with boronic acids, boronate esters, zinc reagent, or tributylstannane reagents in the presence of palladium catalyst to yield the intermediates of formula (X). Using similar reactions as those described in scheme 1, the compounds of formula (X) react with the phenol (IV) to form after hydrolysis under basic aqueous conditions the intermediates of formula (XI), which react with amines of formula (VII) in the presence of a coupling agent, such a HATU, to provide after hydrolysis under basic aqueous conditions the corresponding compounds of formula (I).

The synthesis of the compounds of the invention is illustrated by the following examples including the preparation of the intermediates, which do not limit the scope of the invention in any way.

Abbreviations

In the present application are used the following abbreviations, with the corresponding definitions:

RT: Room Temperature
HATU: N-[(Dimethylamino)-1H-1,2,3-triazolo-[4,5-b]pyridin-1-ylmethylene]-N-methylmethanaminium hexafluorophosphate N-oxide
DIPEA: N,N-Diisopropylethylamine
DMF: Dimethylformamide
DCM: Dichloromethane
THF: Tetrahydrofuran
DMSO: Dimethyl sulfoxide Pharmacological Activity Results The compounds of the present invention were assayed for binding at human EP1, EP2, EP3 and EP4 receptors and were tested at several concentrations for IC50 determination.

Competition Binding in Human EP1 Receptor:

Prostaglandin EP1 receptor competition binding experiments were carried out in a polypropylene 96-well microplate plate with binding buffer (Mes 10 mM, EDTA 1 mM, MgCl2 1 mM, pH=6.0). In each well was incubated 10 µg of membranes from HEK-EP1 cell line and prepared in our laboratory (Lot: A003/19-10-2011, protein concentration=1756 µg/ml), 3 nM [3H]-Prostaglandin E2 (169.8 Ci/mmol, 0.1 mCi/ml, Perkin Elmer NET428250UC) and compounds studied and standard. Non-specific binding was determined in the presence of PGE2 10 µM (Cayman 14010). The reaction mixture (Vt: 250 µl/well) was incubated at 25° C. for 60 min, 200 µL was transferred to GF/C 96-well plate (Millipore, Madrid, Spain) after was filtered and washed four times with 250 µl wash buffer (Mes 10 mM, EDTA 1 mM, MgCl2 1 mM, pH=6.0), before measuring in a microplate beta scintillation counter (Microbeta Trilux, Perkin Elmer, Madrid, Spain) (Abramovitz et al., *Biochim Biophys Acta* 2000; 1483:285-293).

Competition Binding in Human EP2 Receptor:

Prostaglandin EP2 receptor competition binding experiments were carried out in a polypropylene 96-well microplate plate with binding buffer (Hepes 50 mM, CaCl2 1 mM, MgCl2 5 mM, pH=7.4). In each well was incubated 10 µg of membranes from EP2 cell line (Millipore HTS185M, protein concentration=2000 µg/ml), 7.5 nM [3H]-Prostaglandin E2 (169.8 Ci/mmol, 0.1 mCi/ml, Perkin Elmer NET428250UC) and compounds studied and standard. Non-specific binding was determined in the presence of PGE2 200 µM (Cayman 14010). The reaction mixture (Vt: 250 µl/well) was incubated at 25° C. for 90 min, 200 µL was transferred to GF/C 96-well plate (Millipore, Madrid, Spain) after was filtered and washed four times with 250 µl wash buffer (Hepes 50 mM, NaCl 500 mM, pH=7.4), before measuring in a microplate beta scintillation counter (Microbeta Trilux, Perkin Elmer, Madrid, Spain). (Wilson et al., *Br J Pharmacol* 2006; 148:326-339).

Competition Binding in Human EP3 Receptor:

Prostaglandin EP3 receptor competition binding experiments were carried out in a multiscreen GF/C 96-well plate (Millipore, Madrid, Spain) pretreated with binding buffer (Tris-HCl 50 mM, MgCl2 10 mM, EDTA 1 mM, pH=7.4). In each well was incubated 5 µg of membranes from EP3 cell line (Millipore; HTS092M, protein concentration=2000 µg/ml), 1.5 nM [3H]-Prostaglandin E2 (169.8 Ci/mmol, 0.1 mCi/ml, Perkin Elmer NET428250UC) and compounds studied and standard. Non-specific binding was determined in the presence of PGE2 200 µM (Cayman 14010). The reaction mixture (Vt: 250 µl/well) was incubated at 25° C. for 90 min, 200 µL was transferred to GF/C 96-well plate (Millipore, Madrid, Spain) after was filtered and washed four times with 250 µl wash buffer (Tris-HCl 50 mM, pH=7.4), before measuring in a microplate beta scintillation counter (Microbeta Trilux, Perkin Elmer, Madrid, Spain). (Audoly et al., *Mol Pharmacol* 1997; 51:61-68).

Competition Binding in Human EP4 Receptor:

Prostaglandin EP4 receptor competition binding experiments were carried out in a multiscreen GF/B 96-well plate (Millipore, Madrid, Spain) pretreated with binding buffer (Mes 25 mM, EDTA 1 mM, MgCl2 10 mM, pH=6.0). In each well was incubated 35 µg of membranes from HEK-EP4 cell line and prepared in our laboratory (Lot: A003/27-04-2011, protein concentration=2803 µg/ml), 1 nM [3H]-Prostaglandin E2 (169.8 Ci/mmol, 0.1 mCi/ml, Perkin Elmer NET428250UC) and compounds studied and standard. Non-specific binding was determined in the presence of PGE2 10 µM (Cayman 14010). The reaction mixture (Vt: 250 µl/well) was incubated at 25° C. for 120 min, 200 µL was transferred to GF/B 96-well plate (Millipore, Madrid, Spain) after was filtered and washed six times with 250 µl wash buffer (Mes 25 mM, BSA 0.01%, pH=6.0), before measuring in a microplate beta scintillation counter (Microbeta Trilux, Perkin Elmer, Madrid, Spain). (Abramovitz et al., *Biochim Biophys Acta* 2000; 1483:285-293).

The inhibition constants (Ki) were calculated using the Cheng Prusoff equation $$K_i = \frac{IC_{50}}{(1 + L/K_D)}$$

where L=concentration of radioligand in the assay, and KD=affinity of the radioligand for the receptor. A scatchard plot is used to determine the KD.

Compounds of the present invention do not show any significant binding affinity against the receptors EP1 and EP3

Table 1 shows the Ki values of some compounds of the present invention for the receptors EP2 and EP4.

Ki Ranges: A<0, 1 µM; 0, 1 µM<=B<1 µM; 1 µM<=C<10 µM, D>=10 µM

TABLE 1

| Example | Ki values | |
|---|---|---|
| | EP2 | EP4 |
| 1 | D | A |
| 2 | D | A |
| 3 | D | A |
| 4 | A | A |
| 5 | A | A |
| 6 | C | A |
| 7 | C | A |
| 8 | A | A |
| 9 | C | A |
| 10 | C | A |
| 11 | D | B |
| 12 | D | B |
| 13 | A | B |
| 14 | B | C |
| 15 | A | A |
| 18 | C | A |
| 19 | A | A |
| 20 | C | A |
| 21 | A | A |
| 26 | D | A |
| 27 | C | C |
| 28 | C | A |
| 29 | C | A |
| 30 | C | A |
| 31 | C | A |
| 32 | C | A |

As can be seen from the results described in Table 1, the compounds of the present invention bind potently to the EP4 and/or EP2 receptors of prostaglandin E2.

The compounds of the invention are useful in the treatment or prevention of diseases known to be susceptible to improvement by modulation of EP4 and/or EP2 receptors. Such diseases are selected from cancer, pain, inflammation, neurodegerative diseases and kidney diseases.

Thus, the compounds of the invention and salts thereof are used in the manufacture of a medicament for the treatment or prevention of diseases known to be susceptible to improvement by modulation of EP4 and/or EP2 receptors.

Accordingly, the derivatives of the invention and pharmaceutically acceptable salts thereof and pharmaceutical compositions comprising such compounds and/or salts thereof, may be used in a method of treatment or prevention of disorders of the human body known to be susceptible to improvement by modulation of EP4 and/or EP2 receptors, said method comprising administering to a subject requiring such treatment or prevention an effective amount of the N-benzyl-2-phenoxybenzamide derivatives of the invention or a pharmaceutically acceptable salt thereof.

By an "effective amount" or a "therapeutically effective amount" of a compound, drug or pharmacologically active agent is meant a nontoxic but sufficient amount of the compound, drug or agent to provide the desired effect. The amount that is "effective" will vary from subject to subject, depending on the age and general condition of the individual, the particular active agent or agents, and the like. Thus, it is not always possible to specify an exact "effective amount". However, an appropriate "effective" amount in any individual case may be determined by one of ordinary skill in the art using routine experimentation.

One therapeutic use of the compounds of the present invention is to treat proliferative diseases or disorders such as cancer. Cancer is selected from colon cancer, gastric cancer, prostate cancer, lung cancer, hepatocellular carcinoma, renal carcinoma and breast cancer.

The present invention also provides pharmaceutical compositions which comprise, as an active ingredient, at least a N-benzyl-2-phenoxybenzamide derivatives of formula (I) or a pharmaceutically acceptable salt thereof in association with other therapeutics agents and a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably, the compositions are made up in a form suitable for oral, topical, nasal, rectal, percutaneous or injectable administration.

The pharmaceutically acceptable excipients, which are admixed with the active compound or salts of such compound, to form the compositions of this invention, are well known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents, which may be used in the preparation of the compositions, include those liquid and solid diluents, which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The present invention will be further illustrated by the following examples. The following are given by way of illustration and do not limit the scope of the invention in anyway.

EXAMPLES

General. Reagents, solvents and starting products were acquired from commercial sources. The term "concentration" refers to the vacuum evaporation using a Büchi rotavapor. When indicated, the reaction products were purified by "flash" chromatography on silica gel (40-63 μm) with the indicated solvent system. The spectroscopic data were measured in a Varian Mercury 400 spectrometer. The melting points were measured in a Büchi 535 instrument. The HPLC-MS were performed on a Gilson instrument equipped with a Gilson 321 piston pump, a Gilson 864 vacuum degasser, a Gilson 189 injection module, a ¹⁄₁₀₀₀ Gilson splitter, a Gilson 307 pump, a Gilson 170 detector, and a Thermoquest Fennigan aQa detector.

Intermediate 1: methyl 4-(azidomethyl)-3-fluorobenzoate

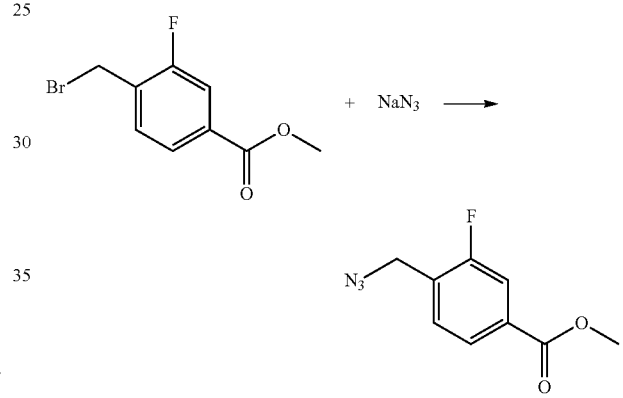

A solution of methyl 4-(bromomethyl)-3-fluorobenzoate (100 mg, 1.0 eq) and sodium azide (29 mg, 1.2 eq) in DMF (1.0 mL) was stirred at 80° C. for 90 min. Once cooled, the reaction was diluted with brine (3 mL) and extracted with ethyl acetate (3×10 mL). The combined organic solution was washed with water (25 mL) and brine (25 mL), dried over Na$_2$SO$_4$, filtered and concentrated under reduced pressure. The desired azide was obtained as pale yellow liquid (quantitative), which was used in the next step without further purification.

$^1$H-NMR (400 MHz, DMSO-d$^6$): δ=7.82 (dd, 1H), 7.74 (dd, 1H), 7.64 (t, 1H), 4.62 (s, 2H), 3.87 (s, 3H).

HPLC-MS: Rt 2.65 m/z 182.0 (MH$^+$)

Intermediate 2: methyl 4-(aminomethyl)-3-fluorobenzoate

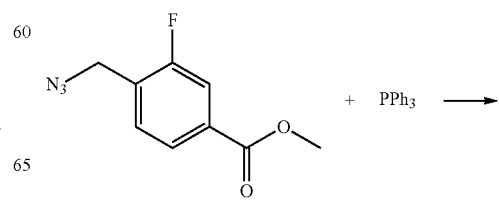

A solution of methyl 4-(azidomethyl)-3-fluorobenzoate (110 mg, 1.0 eq), triphenylphosphine (189 mg, 1.2 eq) and water (0.9 mL) in THF (2 mL) was stirred at room temperature for 20 hours. The solvent was removed under reduced pressure and purification by flash column chromatography (dichloromethane:methanol, 30:1) gave the methyl 4-(aminomethyl)-3-fluorobenzoate as yellow wax (70 mg, 63.7% yield).

$^1$H-NMR (400 MHz, DMSO-d$^6$): δ=7.78 (dd, 1H), 7.67 (t, 1H), 7.61 (dd, 1H), 3.85 (s, 3H), 3.80 (s, 2H), 1.96 (s, 2H).

HPLC-MS: Rt 1.63 m/z 184.1 (MH$^+$)

Intermediate-3: methyl 4-fluoro-[1,1'-biphenyl]-3-carboxylate

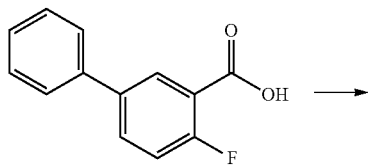

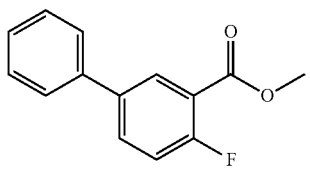

To a solution of 4-fluoro-[1,1'-biphenyl]-3-carboxylic acid (200.0 mg, 0.93 mmol) in methanol (1 mL) was added a catalytic amount of H$_2$SO$_4$ and the reaction was stirred at 70° C. overnight. The solution was partitioned between water and ethyl acetate and the organic layer was washed with NaHCO$_3$ sat and brine. It was dried over anhydrous sodium sulphate, filtered and concentrated to afford intermediate 1 as an oil (167.0 mg, 76.0%).

$^1$H-NMR (400 MHz, DMSO-d$^6$): δ=8.09 (dd, 1H), 7.96 (ddd, 1H), 7.68 (d, 2H), 7.46 (m, 2H), 3.89 (s, 3H).

HPLC-MS: Rt 5.337 m/z 231.0 (MH$^+$)

The following intermediate was synthesized using the procedure described for intermediate 3:

Intermediate 4: methyl 5-bromo-2-fluorobenzoate $^1$H-NMR (400 MHz, DMSO-d$^6$): δ=7.98 (dd, 1H), 7.87 (m, 1H), 7.37 (dd, 1H), 3.86 (s, 3H).

Intermediate 5: methyl 5-bromo-2-(4-fluorophenoxy)benzoate

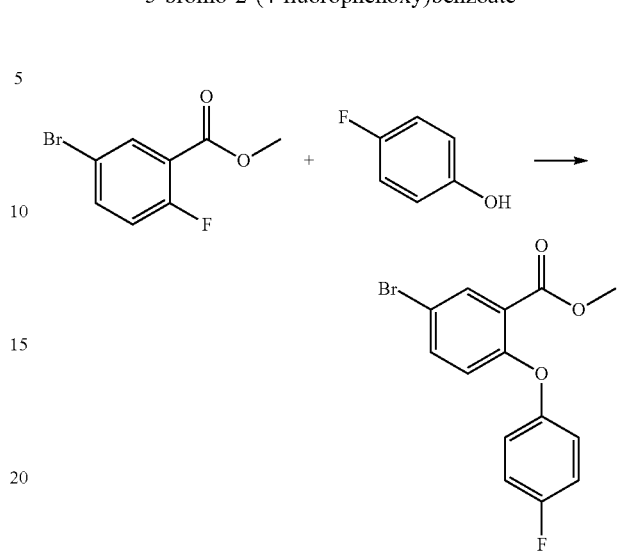

To a stirred solution of 4-fluorophenol (481.0 mg, 4.29 mmol) and sodium hydride (171.6 mg, 4.29 mmol) in N,N-dimethylformamide was added a solution of methyl 5-bromo-2-fluorobenzoate (1000 mg, 4.29 mmol) in N,N-dimethylformamide. The solution was heated at 120° C. and stirred for 16 hours. After cooling to room temperature, the mixture was diluted with water (20 mL) and extracted with ethyl acetate (3×20 mL). The organic layer was dried over sodium sulphate, filtered and concentrated under reduced pressure to afford the titled compound as slight yellow oil (1028.3 mg, 73.7%)

$^1$H-NMR (400 MHz, DMSO-d$^6$): δ=7.95 (d, 1H), 7.75 (dd, 1H), 7.22 (m, 2H), 7.04 (m, 2H), 6.95 (d, 1H), 3.75 (s, 3H).

HPLC-MS: Rt 5.602 m/z 326.9 (MH$^+$)

The following intermediate were synthesized using the procedure described for intermediate 5, and the corresponding methyl esters and 4-fluorophenol:

Intermediate 6: methyl 4-(4-fluorophenoxy)-[1,1'-biphenyl]-3-carboxylate $^1$H-NMR (400 MHz, DMSO-d$^6$): δ=8.07 (d, 1H), 7.88 (dd, 1H), 7.68 (d, 2H), 7.49 (t, 2H), 7.39 (t, 1H), 7.23 (t, 2H), 7.10 (s, 1H), 7.06 (m, 2H), 3.77 (s, 3H).

HPLC-MS: Rt 5.948 m/z 323.0 (MH$^+$)

Intermediate 7: 5-bromo-2-(4-fluorophenoxy)benzoic acid

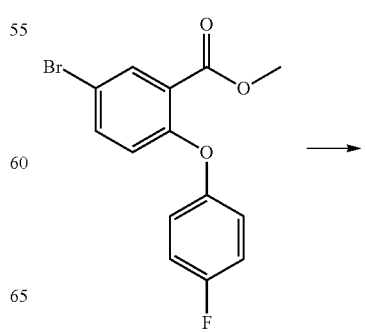

-continued

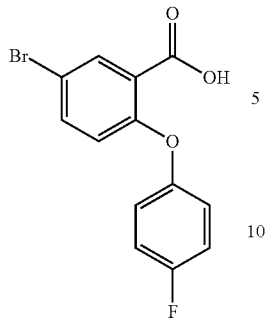

To a solution of methyl 5-bromo-2-(4-fluorophenoxy) benzoate (1101.3 mg, 3.39 mmol) in methanol (8 mL) and THF (8 mL) was added NaOH 2M (8.5 mL, 16.94 mmol) and the mixture was stirred for 3 hours at room temperature. The solution was diluted with water (15 mL) and the pH value was adjusted to 4.0 by the addition of HCl 1M. The mixture was extracted with ethyl acetate (3×50 mL) and the combine organic layer was dried with sodium sulfate and concentrate to afford a white solid that was washed with pentane (823.5 mg, 78.1%).

$^1$H-NMR (400 MHz, DMSO-d$^6$): δ=13.24 (s, 1H), 7.92 (s, 1H), 7.72 (d, 1H), 7.21 (t, 2H), 7.01 (s, 2H), 6.94 (d, 1H).

HPLC-MS: Rt 3.087 m/z 312.9 (MH$^+$)

The following intermediate were synthesized using the procedure described for intermediate 7, and the corresponding methyl esters:

Intermediate 8: 4-(4-fluorophenoxy)-[1,1'-biphenyl]-3-carboxylic acid $^1$H-NMR (400 MHz, DMSO-d$^6$): δ=13.04 (s, 1H), 8.06 (d, 1H), 7.84 (dd, 1H), 7.68 (d, 2H), 7.48 (t, 2H), 7.39 (t, 1H), 7.22 (t, 2H), 7.04 (m, 3H).

HPLC-MS: Rt 3.435 m/z 309.0 (MH$^+$)

Intermediate 9: 4-(4-fluorophenoxy)-3'-(trifluoromethyl)-[1,1'-biphenyl]-3-carboxylic acid $^1$H-NMR (400 MHz, DMSO-d$^6$): δ=13.09 (s, 1H), 8.13 (d, 1H), 7.95 (m, 4H), 7.72 (m, 2H), 7.23 (m, 2H), 7.05 (m, 2H).

HPLC-MS: Rt 2.20 m/z 377.0 (MH$^+$)

Intermediate 10: methyl 4-((5-bromo-2-(4-fluorophenoxy)benzamido)methyl)benzoate

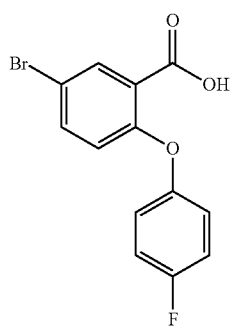

+

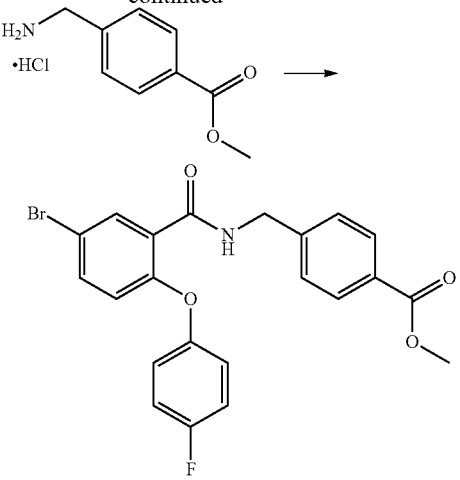

To a solution of 5-bromo-2-(4-fluorophenoxy)benzoic acid (600 mg, 1.93 mmol) in DCM anh. (15 mL) HATU (880.0 mg, 2.30 mmol) and DIPEA (1.31 mL, 7.71 mmol) were added. After the reaction was stirred at RT under N$_2$ during 15 minutes, methyl 4-(aminomethyl)benzoate hydrochloride (466.7 mg, 2.30 mmol) was added and the reaction was allowed to stir overnight at RT. After the addition of 20 mL of H$_2$O, the aqueous phase was extracted with DCM 3×20 mL. The combined organic phase was dried over anhydrous sodium sulfate, filtered, and concentrated to give a white solid (728.5 mg, 82.4%).

$^1$H-NMR (400 MHz, DMSO-d$^6$): δ=8.97 (t, 1H), 7.85 (d, 2H), 7.79 (d, 1H), 7.63 (dd, 1H), 7.38 (d, 2H), 7.24 (t, 2H), 7.11 (dd, 2H), 6.86 (d, 1H), 4.51 (d, 2H), 3.83 (s, 3H).

HPLC-MS: Rt 5.523 m/z 459.0 (MH$^+$)

The following intermediate was synthesized using the procedure described for intermediate 10, and the corresponding chemical reagents or derivatives:

Intermediate 11: methyl (R)-4-(1-(5-bromo-2-(4-fluorophenoxy)benzamido)ethyl) benzoate $^1$H-NMR (400 MHz, DMSO-d$^6$): δ=8.89 (d, 1H), 7.84 (d, 2H), 7.69 (d, 1H), 7.62 (dd, 1H), 7.45 (d, 2H), 7.22 (t, 2H), 7.07 (m, 2H), 6.89 (d, 1H), 5.08 (p, 1H), 3.83 (s, 3H), 1.38 (d, 3H).

HPLC-MS: Rt 3.21 m/z 473.9 (MH$^+$)

Intermediate 12: methyl 4-(1-(5-bromo-2-(4-fluorophenoxy)benzamido)cyclopropyl) benzoate $^1$H-NMR (400 MHz, DMSO-d$^6$): δ=9.13 (s, 1H), 7.78 (s, 1H), 7.76 (d, 2H), 7.65 (dd, 1H), 7.24 (m, 4H), 7.08 (m, 2H), 6.95 (d, 1H), 3.82 (s, 3H), 1.28 (m, 2H), 1.21 (m, 2H).

HPLC-MS: Rt 3.18 m/z 485.9 (MH$^+$)

Intermediate 13: methyl 4-((4-(4-fluorophenoxy)-[1,1-biphenyl]-3-carboxamido)methyl) benzoate $^1$H-NMR (400 MHz, DMSO-d$^6$): δ=8.96 (t, 1H), 7.93 (d, 1H), 7.86 (d, 2H), 7.76 (dd, 1H), 7.68 (d, 2H), 7.48 (t, 2H), 7.39 (m, 3H), 7.25 (t, 2H), 7.13 (m, 2H), 7.00 (d, 1H), 4.54 (d, 2H), 3.84 (s, 3H).

HPLC-MS: Rt 5.843 m/z 456.1 (MH+)

Intermediate 14: 4-((5-bromo-2-(4-fluorophenoxy)benzamido)methyl)benzoic acid

To a solution of methyl 4-((5-bromo-2-(4-fluorophenoxy)benzamido)methyl)benzoate (200 mg, 1.0 eq) in THF (2.0 mL) and methanol (2.0 mL) was added NaOH (2 M) (1.1 mL, 5.0 eq)) and the mixture was stirred for 20 hours at room temperature. After diluting with water (10 mL), the mixture was neutralized with aqueous HCl, filtered and washed with water and pentane to obtain the acid as white solid (176 mg, 90.9% yield).

$^1$H-NMR (400 MHz, DMSO-d$^6$): δ=12.88 (s, 1H), 8.98 (t, 1H), 7.82 (m, 3H), 7.63 (dd, 1H), 7.32 (m, 2H), 7.24 (m, 2H), 7.12 (m, 2H), 6.86 (d, 1H), 4.49 (d, 2H).

HPLC-MS: Rt 1.26 m/z 444.0 (MH+)

Intermediate 15: methyl 4-((2-(4-fluorophenoxy)-5-(pyridin-4-yl)benzamido)methyl) benzoate

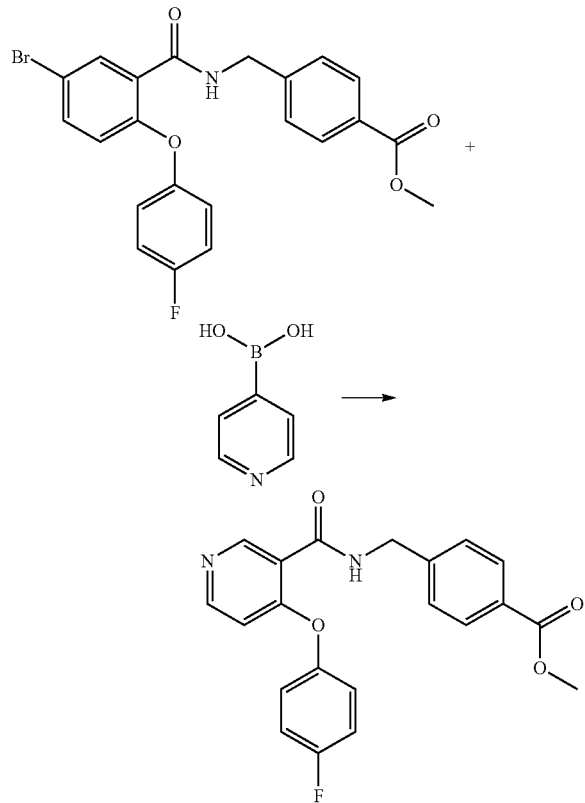

To a solution of methyl 4-((5-bromo-2-(4-fluorophenoxy)benzamido)methyl)benzoate (70.0 mg, 0.15 mmol) in dioxane, pyridine-4-boronic acid (37.6 mg, 0.31 mmol) [1,1'-bis(diphenylphosphino)ferrocene] dichloropalladium (II) (7.5 mg, 0.009 mmol) was added Cs$_2$CO$_3$ 2M (0.23 mL, 0.46 mmol). The mixture was degassed with N$_2$ and stirred at 100° C. overnight. Then, the reaction was filtered through celite and extracted with ethyl acetate. The organic fraction was washed with NaOH 1M, NaHCO$_3$ sat and brine and dried over anhydrous sodium sulfate. The solvent was removed in vacuo and the residue purified using flash chromatography (hexane:Ethyl acetate 1:1). Solvent removal afforded the product as a white solid that was washed with pentane/diethyl ether (44.7 mg, 65.3%).

$^1$H-NMR (400 MHz, DMSO-d$^6$): δ=9.00 (t, 1H), 8.65 (d, 2H), 8.08 (d, 1H), 7.89 (m, 3H), 7.75 (d, 2H), 7.42 (d, 2H), 7.27 (m, 2H), 7.17 (m, 2H), 7.01 (d, 1H), 4.56 (d, 2H), 3.84 (s, 3H).

HPLC-MS: Rt 4.875 m/z 457.1 (MH+)

The following intermediates were synthesized using the procedure described for intermediate 15, using the corresponding chemical reagents or derivatives:

Intermediate 16: methyl 4-((4'-chloro-4-(4-fluorophenoxy)-[1,1'-biphenyl]-3-carboxamido)methyl)benzoate $^1$H-NMR (400 MHz, DMSO-d$^6$): δ=8.99 (t, 1H), 7.92 (d, 1H), 7.85 (d, 2H), 7.74 (m, 3H), 7.51 (t, 2H), 7.39 (d, 2H), 7.25 (t, 2H), 7.12 (m, 2H), 6.99 (d, 1H), 4.53 (d, 2H), 3.83 (s, 3H).

HPLC-MS: Rt 6.203 m/z 490.1 (MH+)

Intermediate 17: methyl 4-((4'-fluoro-4-(4-fluorophenoxy)-[1,1'-biphenyl]-3-carboxamido)methyl)benzoate $^1$H-NMR (400 MHz, DMSO-d$^6$): δ=8.98 (s, 1H), 7.86 (m, 3H), 7.72 (s, 3H), 7.37 (m, 2H), 7.27 (m, 4H), 7.12 (s, 2H), 6.98 (d, 1H), 4.53 (d, 2H), 3.83 (s, 3H).

HPLC-MS: Rt 5.945 m/z 474.1 (MH+)

Intermediate 18: methyl 4-((3'-fluoro-4-(4-fluorophenoxy)-[1,1'-biphenyl]-3-carboxamido)methyl)benzoate $^1$H-NMR (400 MHz, DMSO-d$^6$): δ=8.99 (s, 1H), 7.95 (d, 1H), 7.85 (d, 2H), 7.80 (dd, 1H), 7.53 (t, 3H), 7.40 (d, 2H), 7.24 (dd, 3H), 7.13 (dd, 2H), 6.98 (d, 1H), 4.54 (d, 2H), 3.83 (s, 3H).

HPLC-MS: Rt 5.963 m/z 474.1 (MH+)

Intermediate 19: methyl 4-((2'-fluoro-4-(4-fluorophenoxy)-[1,1'-biphenyl]-3-carboxamido)methyl)benzoate $^1$H-NMR (400 MHz, DMSO-d$^6$): δ=8.99 (s, 1H), 7.85 (d, 3H), 7.64 (d, 1H), 7.57 (s, 1H), 7.40 (d, 3H), 7.30 (m, 4H), 7.17 (s, 2H), 6.98 (d, 1H), 4.54 (d, 2H), 3.83 (s, 3H).

HPLC-MS: Rt 5.936 m/z 474.1 (MH+)

Intermediate 20: methyl 4-((4'-cyano-4-(4-fluorophenoxy)-[1,1'-biphenyl]-3-carboxamido)methyl)benzoate $^1$H-NMR (400 MHz, DMSO-d$^6$): δ=9.01 (t, 1H), 8.02 (d, 1H), 7.93 (m, 4H), 7.85 (m, 3H), 7.41 (d, 2H), 7.27 (t, 2H), 7.16 (m, 2H), 7.00 (d, 1H), 4.55 (d, 2H), 3.83 (s, 3H).

HPLC-MS: Rt 5.649 m/z 481.1 (MH+)

Intermediate 21: methyl 4-((3'-cyano-4-(4-fluorophenoxy)-[1,1'-biphenyl]-3-carboxamido)methyl)benzoate $^1$H-NMR (400 MHz, DMSO-d$^6$): δ=9.00 (t, 1H), 8.20 (s, 1H), 8.04 (dd, 2H), 7.85 (t, 4H), 7.68 (t, 1H), 7.41 (d, 2H), 7.27 (t, 2H), 7.15 (dd, 2H), 7.00 (d, 1H), 4.55 (d, 2H), 3.84 (s, 3H).

HPLC-MS: Rt 5.668 m/z 481.1 (MH+)

Intermediate 22: methyl 4-((2-(4-fluorophenoxy)-5-(3-fluoropyridin-4-yl)benzamido) methyl)benzoate $^1$H-NMR (400 MHz, DMSO-d$^6$): δ=9.03 (t, 1H), 8.67 (d, 1H), 8.51 (d, 1H), 7.97 (s, 1H), 7.86 (d, 2H), 7.77 (d, 1H), 7.68 (dd, 1H), 7.42 (d, 2H), 7.29 (dd, 2H), 7.20 (m, 2H), 7.01 (d, 1H), 4.56 (d, 2H), 3.83 (s, 3H).
HPLC-MS: Rt 5.199 m/z 475.1 (MH$^+$)

Intermediate 23: methyl 4-((2-(4-fluorophenoxy)-5-(pyridin-3-yl)benzamido)methyl) benzoate $^1$H-NMR (400 MHz, DMSO-d$^6$): δ=9.00 (t, 1H), 8.92 (d, 1H), 8.58 (dd, 1H), 8.11 (m, 1H), 7.99 (d, 1H), 7.84 (m, 3H), 7.50 (dd, 1H), 7.41 (d, 2H), 7.26 (t, 2H), 7.14 (m, 2H), 7.02 (d, 1H), 4.54 (d, 2H), 3.83 (s, 3H).
HPLC-MS: Rt 5.015 m/z 457.1 (MH$^+$)

Intermediate 24: methyl 4-((2-(4-fluorophenoxy)-5-(3-chloropyridin-4-yl)benzamido) methyl)benzoate $^1$H-NMR (400 MHz, DMSO-d$^6$): δ=9.02 (t, 1H), 8.75 (s, 1H), 8.59 (d, 1H), 7.86 (d, 2H), 7.84 (d, 1H), 7.64 (dd, 1H), 7.53 (d, 1H), 7.42 (d, 2H), 7.30 (t, 2H), 7.21 (m, 2H), 6.98 (d, 1H), 4.55 (d, 2H), 3.83 (s, 3H).
HPLC-MS: Rt 5.378 m/z 491.1 (MH$^+$)

Intermediate 25: methyl 4-((2-(4-fluorophenoxy)-5-(pyrimidin-5-yl)benzamido)methyl) benzoate $^1$H-NMR (400 MHz, DMSO-d$^6$): δ=9.18 (m, 3H), 9.02 (t, 1H), 8.08 (d, 1H), 7.88 (m, 3H), 7.42 (d, 2H), 7.27 (t, 2H), 7.15 (m, 2H), 7.04 (d, 1H), 4.55 (d, 2H), 3.83 (s, 3H).
HPLC-MS: Rt 4.715 m/z 458.1 (MH$^+$)

Intermediate 26: methyl 4-((3',4'-difluoro-4-(4-fluorophenoxy)-[1,1'-biphenyl]-3-carboxamido)methyl) benzoate $^1$H-NMR (400 MHz, DMSO-d$^6$): δ=8.98 (t, 1H), 7.95 (d, 1H), 7.81 (m, 4H), 7.53 (m, 2H), 7.40 (d, 2H), 7.26 (t, 2H), 7.13 (m, 2H), 6.98 (d, 1H), 4.54 (d, 2H), 3.83 (s, 3H).
HPLC-MS: Rt 5.977 m/z 492.1 (MH$^+$)

Intermediate 27: methyl 4-((4-(4-fluorophenoxy)-4'-(trifluoromethyl)-[1,1'-biphenyl]-3-carboxamido) methyl)benzoate $^1$H-NMR (400 MHz, DMSO-d$^6$): δ=9.02 (t, 1H), 8.01 (d, 1H), 7.93 (d, 2H), 7.84 (m, 5H), 7.41 (d, 2H), 7.27 (dd, 2H), 7.16 (m, 2H), 7.01 (d, 1H), 4.55 (d, 2H), 3.83 (s, 3H).
HPLC-MS: Rt 6.223 m/z 524.1 (MH$^+$)

Intermediate 28: methyl 4-((4-(4-fluorophenoxy)-3'-(trifluoromethyl)-[1,1'-biphenyl]-3-carboxamido) methyl)benzoate $^1$H-NMR (400 MHz, DMSO-d$^6$): δ=9.00 (t, 1H), 8.01 (m, 3H), 7.85 (d, 3H), 7.71 (m, 2H), 7.40 (d, 2H), 7.26 (t, 2H), 7.15 (dd, 2H), 7.01 (d, 1H), 4.55 (d, 2H), 3.83 (s, 3H).
HPLC-MS: Rt 6.199 m/z 524.1 (MH$^+$)

Intermediate 29: methyl 4-((2-(4-fluorophenoxy)-5-(thiophen-2-yl)benzamido)methyl) benzoate $^1$H-NMR (400 MHz, DMSO-d$^6$): δ=8.99 (t, 1H), 7.90 (d, 1H), 7.85 (d, 2H), 7.74 (dd, 1H), 7.56 (d, 1H), 7.52 (d, 1H), 7.39 (d, 2H), 7.25 (t, 2H), 7.13 (m, 3H), 6.95 (d, 1H), 4.52 (d, 2H), 3.83 (s, 3H).
HPLC-MS: Rt 3.21 m/z 462.1 (MH$^+$)

Intermediate 30: methyl 4-((3',5'-difluoro-4-(4-fluorophenoxy)-[1,1'-biphenyl]-3-carboxamido)methyl) benzoate $^1$H-NMR (400 MHz, DMSO-d$^6$): δ=9.00 (t, 1H), 8.00 (d, 1H), 7.84 (m, 3H), 7.48 (m, 2H), 7.41 (d, 2H), 7.25 (m, 3H), 7.14 (m, 2H), 6.97 (d, 1H), 4.54 (d, 2H), 3.83 (s, 3H).
HPLC-MS: Rt 3.31 m/z 492.21 (MH$^+$)

Intermediate 31: methyl 4-((3'-chloro-4-(4-fluorophenoxy)-[1,1'-biphenyl]-3-carboxamido)methyl) benzoate $^1$H-NMR (400 MHz, DMSO-d$^6$): δ=8.99 (t, 1H), 7.96 (d, 1H), 7.86 (d, 2H), 7.80 (dd, 1H), 7.76 (m, 1H), 7.66 (d, 1H), 7.50 (t, 1H), 7.43 (m, 3H), 7.25 (m, 2H), 7.14 (m, 2H), 6.87 (d, 1H), 4.54 (d, 2H), 3.83 (s, 3H).
HPLC-MS: Rt 3.41 m/z 490.16 (MH$^+$)

Intermediate 32: methyl 4-((3'-fluoro-4-(4-fluorophenoxy)-5'-(trifluoromethyl)-[1,1'-biphenyl]-3-carboxamido)methyl)benzoate $^1$H-NMR (400 MHz, DMSO-d$^6$): δ=9.01 (t, 1H), 8.06 (d, 1H), 7.95 (d, 1H), 7.88 (m, 4H), 7.67 (d, 1H), 7.41 (d, 2H), 7.26 (m, 2H), 7.15 (m, 2H), 7.00 (d, 1H), 4.55 (d, 2H), 3.83 (s, 3H).
HPLC-MS: Rt 3.48 m/z 542.21 (MH$^+$)

Intermediate 33: methyl 4-((3'-cyano-5'-fluoro-4-(4-fluorophenoxy)-[1,1'-biphenyl]-3-carboxamido) methyl)benzoate $^1$H-NMR (400 MHz, DMSO-d$^6$): δ=9.00 (t, 1H), 8.12 (s, 1H), 8.07 (d, 1H), 8.00 (m, 1H), 7.88 (m, 4H), 7.42 (d, 2H), 7.26 (m, 2H), 7.15 (m, 2H), 6.99 (d, 1H), 4.53 (d, 2H), 3.83 (s, 3H).
HPLC-MS: Rt 3.13 m/z 499.21 (MH$^+$)

Intermediate 34: methyl 4-((3'-chloro-5'-cyano-4-(4-fluorophenoxy)-[1,1'-biphenyl]-3-carboxamido) methyl)benzoate $^1$H-NMR (400 MHz, DMSO-d$^6$): δ=9.00 (t, 1H), 8.22 (d, 1H), 8.16 (t, 1H), 8.05 (m, 2H), 7.87 (m, 3H), 7.42 (d, 2H), 7.27 (m, 2H), 7.15 (m, 2H), 6.98 (d, 1H), 4.55 (d, 2H), 3.84 (s, 3H).
HPLC-MS: Rt 3.26 m/z 515.1 (MH$^+$)

Intermediate 35: methyl 4-((2-(4-fluorophenoxy)-5-(1H-pyrazol-4-yl)benzamido)methyl) benzoate $^1$H-NMR (400 MHz, DMSO-d$^6$): δ=12.83 (s, 1H), 8.99 (t, 1H), 7.82 (m, 4H), 7.62 (m, 2H), 7.36 (dd, 2H), 7.24 (m, 2H), 7.12 (m, 2H), 6.86 (d, 1H), 4.50 (d, 2H), 3.83 (s, 3H).
HPLC-MS: Rt 2.03 m/z 446.0 (MH$^+$)

Intermediate 36: methyl 4-((2-(4-fluorophenoxy)-5-(1-methyl-1H-pyrazol-4-yl) benzamido)methyl)benzoate $^1$H-NMR (400 MHz, DMSO-d$^6$): δ=8.92 (t, 1H), 8.18 (s, 1H), 7.84 (m, 4H), 7.64 (dd, 1H), 7.37 (d, 2H), 7.21 (m, 2H), 7.06 (m, 2H), 6.93 (d, 1H), 4.51 (d, 2H), 3.86 (s, 3H), 3.83 (s, 3H).
HPLC-MS: Rt 2.70 m/z 460.2 (MH$^+$)

Intermediate 37: methyl 4-((2-(4-fluorophenoxy)-5-(1-methyl-1H-pyrazol-5-yl) benzamido)methyl)benzoate $^1$H-NMR (400 MHz, DMSO-d$^6$): δ=9.01 (t, 1H), 7.85 (d, 2H), 7.77 (d, 1H), 7.61 (dd, 1H), 7.48 (d, 1H), 7.40 (d, 2H), 7.26 (m, 2H), 7.17 (m, 2H), 6.98 (d, 1H), 6.43 (d, 1H), 4.54 (d, 2H), 3.86 (s, 3H), 3.83 (s, 3H).
HPLC-MS: Rt 2.73 m/z 460.13 (MH$^+$)

Intermediate 38: methyl 4-((4-(4-fluorophenoxy)-3'-(pyridin-4-yl)-[1,1'-biphenyl]-3-ylcarboxamido)methyl)benzoate $^1$H-NMR (400 MHz, DMSO-d$^6$): δ=9.00 (t, 1H), 8.66 (dd, 2H), 8.06 (m, 2H), 7.85 (m, 7H), 7.63 (t, 1H), 7.40 (d, 2H), 7.25 (m, 2H), 7.14 (m, 2H), 7.02 (d, 1H), 4.55 (d, 2H), 3.83 (s, 3H).
HPLC-MS: Rt 3.06 m/z 533.2 (MH$^+$)

Intermediate 39: methyl 4-((5-(5-cyanofuran-2-yl)-2-(4-fluorophenoxy)benzamido) methyl)benzoate $^1$H-NMR (400 MHz, DMSO-d$^6$): δ=9.02 (t, 1H), 8.10 (s, 1H), 7.87 (m, 3H), 7.42 (m, 3H), 7.28 (m, 4H), 7.18 (m, 2H), 6.97 (d, 1H), 4.55 (d, 2H), 3.83 (s, 3H).
HPLC-MS: Rt 3.08 m/z 471.1 (MH$^+$)

Intermediate 40: methyl 3-fluoro-4-((4-(4-fluorophenoxy)-3'-(trifluoromethyl)-[1,1'-biphenyl]-3-yl-carboxamido)methyl)benzoate $^1$H-NMR (400 MHz, DMSO-d$^6$): δ=9.01 (t, 1H), 8.01 (m, 2H), 7.86 (dd, 1H), 7.74 (dd, 2H), 7.67 (m, 2H), 7.44 (t, 1H), 7.25 (m, 2H), 7.15 (m, 2H), 7.01 (d, 1H), 4.55 (d, 2H), 3.85 (s, 3H).

Intermediate 41: methyl (R)-4-(1-(4-(4-fluorophenoxy)-3'-(trifluoromethyl)-[1,1-biphenyl]-3-carboxamido)ethyl)benzoate $^1$H-NMR (400 MHz, DMSO-d$^6$): δ=8.89 (d, 1H), 8.01 (m, 2H), 7.91 (d, 1H), 7.84 (m, 3H), 7.72 (m, 2H), 7.48 (d, 2H), 7.24 (t, 2H), 7.11 (m, 2H), 7.03 (d, 1H), 5.14 (p, 1H), 3.83 (s, 3H), 1.41 (d, 3H).
HPLC-MS: Rt 3.51 m/z 538.0 (MH$^+$)

Intermediate 42: methyl 4-(1-(4-(4-fluorophenoxy)-3'-(trifluoromethyl)-[1,1'-biphenyl]-3-carboxamido)cyclopropyl)benzoate $^1$H-NMR (400 MHz, DMSO-d$^6$): δ=9.13 (s, 1H), 8.04 (d, 2H), 7.96 (d, 1H), 7.86 (dd, 1H), 7.75 (m, 4H), 7.27 (m, 4H), 7.13 (dd, 2H), 7.09 (d, 1H), 3.82 (s, 3H), 1.32 (t, 2H), 1.25 (t, 2H).
HPLC-MS: Rt 3.48 m/z 550.0 (MH$^+$)

Intermediate 43: methyl 4-((2-(4-fluorophenoxy)-5-(pyridin-2-yl)benzamido)methyl) benzoate To a solution of methyl 4-((5-bromo-2-(4-fluorophenoxy)benzamido)methyl)benzoate (100.0 mg, 0.22 mmol) and tetrakis(triphenylphosphine)palladium(0) (15.1 mg, 0.013 mmol) in dry dioxane (1.5 mL), was added 2-(tributylstannyl)pyridine (113.4 mg, 0.26 mmol). The mixture was purged with N$_2$ and stirred during 2 days at room temperature. The reaction was diluted with ethyl acetate and washed with NaOH 2M. The organic layer was dried over anhydrous sodium sulfate, filtered and concentrated and the residue was purified by flash chromatography (hexane:Ethyl acetate 1:1) to give a white solid. The product was washed with pentane/diethyl ether (40.3 mg, 40.5%)

$^1$H-NMR (400 MHz, DMSO-d$^6$): δ=9.00 (t, 1H), 8.66 (d, 1H), 8.39 (d, 1H), 8.16 (dd, 1H), 7.98 (d, 1H), 7.90 (dd, 1H), 7.86 (d, 2H), 7.42 (d, 2H), 7.36 (dd, 1H), 7.27 (t, 2H), 7.17 (dd, 2H), 6.98 (d, 1H), 4.56 (d, 2H), 3.84 (s, 3H).
HPLC-MS: Rt 5.308 m/z 457.1 (MH$^+$)

The following intermediate was synthesized using the procedure described for intermediate 43, and the corresponding chemical reagents or derivatives:

Intermediate 44: methyl 4-((2-(4-fluorophenoxy)-5-(pyrimidin-4-yl)benzamido)methyl) benzoate $^1$H-NMR (400 MHz, DMSO-d$^6$): δ=9.24 (d, 1H), 9.04 (t, 1H), 8.86 (d, 1H), 8.51 (d, 1H), 8.29 (dd, 1H), 8.12 (dd, 1H), 7.87 (d, 2H), 7.44 (d, 2H), 7.30 (m, 2H), 7.22 (m, 2H), 7.00 (d, 1H), 4.57 (d, 2H), 3.83 (s, 3H).
HPLC-MS: Rt 4.890 m/z 458.1 (MH$^+$)

Example 1: 4-((2-(4-fluorophenoxy)-5-(pyridin-4-yl)benzamido)methyl)benzoic acid

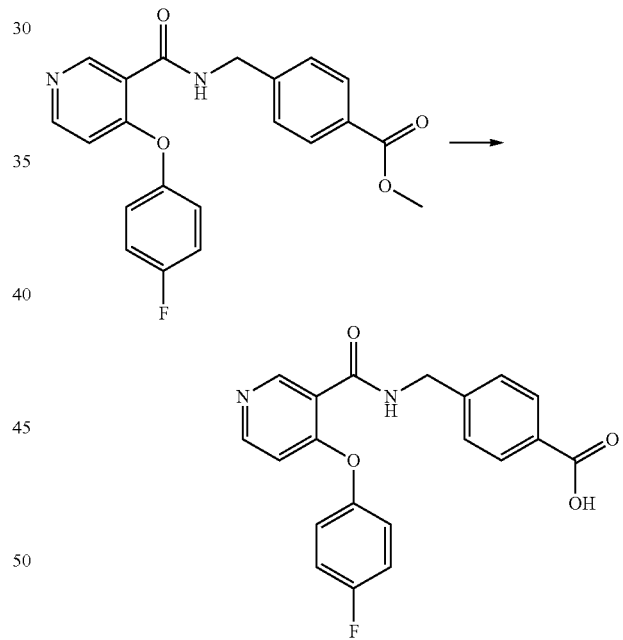

To a solution of methyl 4-((2-(4-fluorophenoxy)-5-(pyridin-4-yl)benzamido)methyl)benzoate (35.0 mg, 0.077 mmol) in methanol (0.5 mL) and THF (0.5 mL) was added NaOH 2M (0.19 mL, 0.38 mmol) and the mixture was stirred overnight at room temperature. The solution was diluted with water (15 mL) and the pH value was adjusted to 4.0 by the addition of HCl 1M and the precipitate was filtered and washed with pentane (27.8 mg, 82.0%).

$^1$H-NMR (400 MHz, DMSO-d$^6$): δ=12.85 (s, 1H), 9.01 (t, 1H), 8.64 (d, 2H), 8.07 (d, 1H), 7.90 (dd, 1H), 7.84 (d, 2H), 7.74 (d, 2H), 7.39 (d, 2H), 7.27 (t, 2H), 7.17 (dd, 2H), 7.01 (d, 1H), 4.55 (d, 2H).
HPLC-MS: Rt 3.362 m/z 443.1 (MH$^+$)

The following intermediate were synthesized using the procedure described for Example 1, and the corresponding chemical reagents or derivatives:

Example 2: 4-((4-(4-fluorophenoxy)-[1,1'-biphenyl]-3-carboxamido)methyl)benzoic acid $^1$H-NMR (400 MHz, DMSO-d$^6$): δ=12.84 (s, 1H), 8.95 (s, 1H), 7.93 (d, 1H), 7.83 (d, 2H), 7.76 (dd, 1H), 7.68 (d, 2H), 7.48 (t, 2H), 7.38 (t, 3H), 7.25 (t, 2H), 7.13 (m, 2H), 7.00 (d, 1H), 4.53 (d, 2H).
HPLC-MS: Rt 3.867 m/z 442.1 (MH$^+$)

Example 3: 4-((4'-chloro-4-(4-fluorophenoxy)-[1,1'-biphenyl]-3-carboxamido)methyl) benzoic acid $^1$H-NMR (400 MHz, DMSO-d$^6$): δ=12.88 (s, 1H), 8.97 (t, 1H), 7.93 (d, 1H), 7.83 (d, 2H), 7.75 (m, 3H), 7.53 (d, 2H), 7.37 (d, 2H), 7.26 (t, 2H), 7.13 (m, 2H), 6.99 (d, 1H), 4.53 (d, 2H).
HPLC-MS: Rt 4.221 m/z 476.0 (MH$^+$)

Example 4: 4-((4'-fluoro-4-(4-fluorophenoxy)-[1,1'-biphenyl]-3-carboxamido)methyl) benzoic acid $^1$H-NMR (400 MHz, DMSO-d$^6$): δ=12.87 (s, 1H), 8.97 (t, 1H), 7.90 (d, 1H), 7.83 (d, 2H), 7.73 (m, 3H), 7.36 (d, 2H), 7.29 (m, 4H), 7.12 (m, 2H), 6.99 (d, 1H), 4.53 (d, 2H).
HPLC-MS: Rt 4.029 m/z 460.1 (MH$^+$)

Example 5: 4-((3'-fluoro-4-(4-fluorophenoxy)-[1,1'-biphenyl]-3-carboxamido)methyl) benzoic acid $^1$H-NMR (400 MHz, DMSO-d$^6$): δ=12.88 (s, 1H), 8.98 (t, 1H), 7.96 (d, 1H), 7.81 (m, 3H), 7.53 (m, 3H), 7.37 (d, 2H), 7.22 (m, 3H), 7.14 (m, 2H), 6.99 (d, 1H), 4.53 (d, 2H).
HPLC-MS: Rt 4.033 m/z 460.1 (MH$^+$)

Example 6: 4-((2'-fluoro-4-(4-fluorophenoxy)-[1,1'-biphenyl]-3-carboxamido)methyl) benzoic acid $^1$H-NMR (400 MHz, DMSO-d$^6$): δ=12.87 (s, 1H), 8.98 (s, 1H), 7.83 (s, 3H), 7.64 (d, 1H), 7.57 (s, 1H), 7.34 (m, 7H), 7.18 (s, 2H), 6.99 (d, 1H), 4.53 (d, 2H).
HPLC-MS: Rt 4.001 m/z 460.1 (MH$^+$)

Example 7: 4-((4'-cyano-4-(4-fluorophenoxy)-[1,1'-biphenyl]-3-carboxamido)methyl) benzoic acid $^1$H-NMR (400 MHz, DMSO-d$^6$): δ=12.88 (s, 1H), 9.00 (t, 1H), 8.02 (s, 1H), 7.91 (m, 4H), 7.84 (d, 3H), 7.38 (d, 2H), 7.27 (t, 2H), 7.16 (m, 2H), 7.00 (d, 1H), 4.54 (d, 2H).
HPLC-MS: Rt 3.864 m/z 467.1 (MH$^+$)

Example 8: 4-((3'-cyano-4-(4-fluorophenoxy)-[1,1'-biphenyl]-3-carboxamido)methyl) benzoic acid $^1$H-NMR (400 MHz, DMSO-d$^6$): δ=12.88 (s, 1H), 8.99 (t, 1H), 8.20 (s, 1H), 8.04 (dd, 2H), 7.84 (d, 4H), 7.68 (t, 1H), 7.38 (d, 2H), 7.27 (t, 2H), 7.15 (dd, 2H), 7.00 (d, 1H), 4.54 (d, 2H).
HPLC-MS: Rt 3.860 m/z 467.1 (MH$^+$)

Example 9: 4-((2-(4-fluorophenoxy)-5-(3-fluoropyridin-4-yl)benzamido)methyl)benzoic acid $^1$H-NMR (400 MHz, DMSO-d$^6$): δ=12.88 (s, 1H), 9.01 (t, 1H), 8.67 (d, 1H), 8.51 (d, 1H), 7.97 (s, 1H), 7.84 (d, 2H), 7.77 (d, 1H), 7.68 (dd, 1H), 7.39 (d, 2H), 7.29 (t, 2H), 7.20 (m, 2H), 7.01 (d, 1H), 4.55 (d, 2H).
HPLC-MS: Rt 3.495 m/z 461.1 (MH$^+$)

Example 10: 4-((2-(4-fluorophenoxy)-5-(pyridin-3-yl)benzamido)methyl)benzoic acid $^1$H-NMR (400 MHz, DMSO-d$^6$): δ=12.88 (s, 1H), 8.99 (s, 1H), 8.92 (d, 1H), 8.58 (dd, 1H), 8.11 (m, 1H), 7.99 (d, 1H), 7.83 (m, 3H), 7.50 (dd, 1H), 7.38 (d, 2H), 7.26 (t, 2H), 7.15 (m, 2H), 7.02 (d, 1H), 4.54 (d, 2H).
HPLC-MS: Rt 3.390 m/z 443.1 (MH$^+$)

Example 11: 4-((2-(4-fluorophenoxy)-5-(3-chloropyridin-4-yl)benzamido)methyl)benzoic acid $^1$H-NMR (400 MHz, DMSO-d$^6$): δ=12.88 (s, 1H), 9.01 (t, 1H), 8.75 (s, 1H), 8.59 (d, 1H), 7.83 (dd, 3H), 7.64 (dd, 1H), 7.53 (d, 1H), 7.39 (d, 2H), 7.30 (t, 2H), 7.21 (dd, 2H), 6.98 (d, 1H), 4.54 (d, 2H).
HPLC-MS: Rt 3.624 m/z 477.0 (MH$^+$)

Example 12: 4-((2-(4-fluorophenoxy)-5-(pyrimidin-5-yl)benzamido)methyl)benzoic acid $^1$H-NMR (400 MHz, DMSO-d$^6$): δ=12.88 (s, 1H), 9.17 (m, 3H), 9.01 (t, 1H), 8.08 (d, 1H), 7.88 (m, 3H), 7.42 (d, 2H), 7.27 (t, 2H), 7.15 (m, 2H), 7.04 (d, 1H), 4.54 (d, 2H).
HPLC-MS: Rt 3.147 m/z 444.1 (MH$^+$)

Example 13: 4-((3',4'-difluoro-4-(4-fluorophenoxy)-[1,1'-biphenyl]-3-carboxamido) methyl)benzoic acid $^1$H-NMR (400 MHz, DMSO-d$^6$): δ=12.89 (s, 1H), 8.97 (t, 1H), 7.95 (d, 1H), 7.79 (m, 4H), 7.54 (m, 2H), 7.37 (d, 2H), 7.26 (t, 2H), 7.13 (dd, 2H), 6.98 (d, 1H), 4.53 (d, 2H).
HPLC-MS: Rt 4.084 m/z 478.1 (MH$^+$)

Example 14: 4-((4-(4-fluorophenoxy)-4'-(trifluoromethyl)-[1,1'-biphenyl]-3-carboxamido) methyl)benzoic acid $^1$H-NMR (400 MHz, DMSO-d$^6$): δ=12.88 (s, 1H), 9.00 (t, 1H), 8.01 (d, 1H), 7.93 (d, 2H), 7.83 (dd, 5H), 7.38 (d, 2H), 7.27 (t, 2H), 7.16 (m, 2H), 7.02 (d, 1H), 4.54 (d, 2H).
HPLC-MS: Rt 2.53 m/z 510.57 (MH$^+$)

Example 15: 4-((4-(4-fluorophenoxy)-3'-(trifluoromethyl)-[1,1'-biphenyl]-3-carboxamido) methyl)benzoic acid $^1$H-NMR (400 MHz, DMSO-d$^6$): δ=δ=12.88 (s, 1H), 9.01 (t, 1H), 8.01 (dd, 3H), 7.84 (dd, 3H), 7.72 (q, 2H), 7.37 (d, 2H), 7.60 (m, 2H), 7.15 (m, 2H), 7.01 (d, 1H), 4.54 (d, 2H).
HPLC-MS: Rt 2.47 m/z 510.51 (MH$^+$)

Example 16: 4-((2-(4-fluorophenoxy)-5-(pyridin-2-yl)benzamido)methyl)benzoic acid $^1$H-NMR (400 MHz, DMSO-d$^6$): δ=12.88 (s, 1H), 8.99 (t, 1H), 8.67 (d, 1H), 8.39 (d, 1H), 8.16 (dd, 1H), 7.99 (d, 1H), 7.89 (m, 1H), 7.84 (d, 2H), 7.39 (d, 2H), 7.35 (m, 1H), 7.27 (t, 2H), 7.17 (dd, 2H), 6.99 (d, 1H), 4.55 (d, 2H).
HPLC-MS: Rt 3.502 m/z 433.1 (MH$^+$)

Example 17: 4-((2-(4-fluorophenoxy)-5-(pyrimidin-4-yl)benzamido)methyl)benzoic acid $^1$H-NMR (400 MHz, DMSO-d$^6$): δ=12.88 (s, 1H), 9.24 (d, 1H), 9.03 (t, 1H), 8.86 (d, 1H), 8.51 (d, 1H), 8.28 (dd,

Example 18: 4-((2-(4-fluorophenoxy)-5-(thiophen-2-yl)benzamido)methyl)benzoic acid 1H), 8.12 (dd, 1H), 7.85 (d, 2H), 7.41 (d, 2H), 7.30 (m, 2H), 7.22 (dd, 2H), 7.00 (d, 1H), 4.56 (d, 2H).
HPLC-MS: Rt 3.243 m/z 444.1 (MH⁺)

Example 18: 4-((2-(4-fluorophenoxy)-5-(thiophen-2-yl)benzamido)methyl)benzoic acid ¹H-NMR (400 MHz, DMSO-d⁶): δ=12.88 (s, 1H), 8.98 (t, 1H), 7.90 (d, 1H), 7.82 (dd, 2H), 7.73 (dd, 1H), 7.56 (d, 1H), 7.53 (dd, 1H), 7.35 (2H), 7.24 (t, 2H), 7.12 (m, 3H), 6.96 (d, 1H), 4.52 (d, 2H).
HPLC-MS: Rt 2.18 m/z 448.1 (MH⁺)

Example 19: 4-((3',5'-difluoro-4-(4-fluorophenoxy)-[1,1'-biphenyl]-3-carboxamido) methyl)benzoic acid ¹H-NMR (400 MHz, DMSO-d⁶): δ=12.87 (s, 1H), 8.99 (t, 1H), 8.00 (d, 1H), 7.83 dd, 3H), 7.49 (m, 2H), 7.38 (d, 2H), 7.25 (m, 3H), 7.14 (m, 2H), 6.98 (d, 1H), 4.54 (d, 2H).
HPLC-MS: Rt 2.30 m/z 478.17 (MH⁺)

Example 20: 4-((3'-chloro-4-(4-fluorophenoxy)-[1,1'-biphenyl]-3-carboxamido)methyl) benzoic acid ¹H-NMR (400 MHz, DMSO-d⁶): δ=12.88 (s, 1H), 8.99 (t, 1H), 7.97 (d, 1H), 7.80 (m, 4H), 7.68 (d, 1H), 7.51 (t, 1H), 7.46 (m, 1H), 7.39 (d, 2H), 7.27 (m, 2H), 7.15 (m, 2H), 7.00 (d, 1H), 4.55 (d, 2H).
HPLC-MS: Rt 2.86 m/z 476.13 (MH⁺)

Example 21: 4-((3'-fluoro-4-(4-fluorophenoxy)-5'-(trifluoromethyl)-[1,1'-biphenyl]-3-carboxamido)methyl)benzoic acid ¹H-NMR (400 MHz, DMSO-d⁶): δ=12.89 (s, 1H), 9.01 (t, 1H), 8.08 (d, 1H), 7.96 (d, 1H), 7.90 (m, 2H), 7.84 (d, 2H), 7.70 (d, 1H), 7.39 (d, 2H), 7.28 (m, 2H), 7.17 (m, 2H), 7.01 (d, 1H), 4.56 (d, 2H).
HPLC-MS: Rt 2.46 m/z 528.19 (MH⁺)

Example 22: 4-((3'-carbamoyl-5'-chloro-4-(4-fluorophenoxy)-[1,1'-biphenyl]-3-yl carboxamido)methyl)benzoic acid ¹H-NMR (400 MHz, DMSO-d⁶): δ=12.89 (s, 1H), 9.00 (t, 1H), 8.26 (s, 1H), 8.15 (s, 1H), 8.05 (d, 1H), 7.94 (m, 1H), 7.88 (m, 1H), 7.84 (m, 2H), 7.63 (s, 1H), 7.38 (d, 2H), 7.26 (m, 2H), 7.15 (m, 2H), 7.01 (d, 1H), 4.54 (d, 2H).
HPLC-MS: Rt 1.96 m/z 519.07 (MH⁺)

Example 23: 4-((2-(4-fluorophenoxy)-5-(1H-pyrazol-4-yl)benzamido)methyl)benzoic acid ¹H-NMR (400 MHz, DMSO-d⁶): δ=12.96 (s, 1H), 8.90 (t, 1H), 8.09 (s, 2H), 7.85 (d, 1H), 7.81 (m, 2H), 7.69 (dd, 1H), 7.33 (m, 2H), 7.22 (m, 2H), 7.06 (m, 2H), 6.94 (d, 1H), 4.49 (d, 2H).
HPLC-MS: Rt 1.06 m/z 432.1 (MH⁺)

Example 24: 4-((2-(4-fluorophenoxy)-5-(1-methyl-1H-pyrazol-4-yl)benzamido)methyl) benzoic acid ¹H-NMR (400 MHz, DMSO-d⁶): δ=12.88 (s, 1H), 8.91 (t, 1H), 8.18 (s, 1H), 7.88 (s, 1H), 7.81 (m, 3H), 7.64 (dd, 1H), 7.33 (d, 2H), 7.22 (m, 2H), 7.06 (m, 2H), 6.94 (d, 1H), 4.50 (d, 2H), 3.86 (s, 3H).
HPLC-MS: Rt 1.78 m/z 446.10 (MH⁺)

Example 25: 4-((2-(4-fluorophenoxy)-5-(1-methyl-1H-pyrazol-5-yl)benzamido)methyl) benzoic acid ¹H-NMR (400 MHz, DMSO-d⁶): δ=12.88 (s, 1H), 9.00 (t, 1H), 7.83 (d, 2H), 7.77 (d, 1H), 7.61 (dd, 1H), 7.48 (d, 1H), 7.37 (d, 2H), 7.27 (m, 2H), 7.17 (m, 2H), 6.98 (d, 1H), 6.43 (t, 1H), 4.53 (d, 2H), 3.86 (s, 3H).
HPLC-MS: Rt 1.82 m/z 446.10 (MH⁺)

Example 26: 4-((4-(4-fluorophenoxy)-3'-(pyridin-4-yl)-[1,1'-biphenyl]-3-ylcarboxamido) methyl)benzoic acid ¹H-NMR (400 MHz, DMSO-d⁶): δ=12.88 (s, 1H), 9.02 (t, 1H), 8.92 (d, 1H), 8.38 (d, 2H), 8.25 (s, 1H), 8.10 (d, 1H), 7.98 (d, 1H), 7.92 (d, 2H), 7.83 (d, 2H), 7.71 (t, 1H), 7.38 (d, 2H), 7.27 (m, 2H), 7.15 (m, 2H), 7.04 (d, 1H), 4.54 (d, 2H).
HPLC-MS: Rt 2.15 m/z 519.2 (MH⁺)

Example 27: 4-((5-(5-carbamoylfuran-2-yl)-2-(4-fluorophenoxy)benzamido)methyl) benzoic acid ¹H-NMR (400 MHz, DMSO-d⁶): δ=12.89 (s, 1H), 9.00 (t, 1H), 8.17 (t, 1H), 8.02 (s, 1H), 7.94 (m, 2H), 7.45 (s, 2H), 7.37 (t, 2H), 7.26 (m, 2H), 7.13 (m, 3H), 6.99 (d, 1H), 4.53 (d, 2H).
HPLC-MS: Rt 1.74 m/z 475.0 (MH⁺)

Example 28: 3-fluoro-4-((4-(4-fluorophenoxy)-3'-(trifluoromethyl)-[1,1'-biphenyl]-3-ylcarboxamido)methyl)benzoic acid ¹H-NMR (400 MHz, DMSO-d⁶): δ=13.26 (s, 1H), 9.00 (t, 1H), 8.00 (m, 3H), 7.86 (dd, 1H), 7.73 (m, 2H), 7.63 (m, 2H), 7.41 (t, 1H), 7.26 (m, 2H), 7.15 (m, 2H), 7.00 (d, 1H), 4.54 (d, 2H).
HPLC-MS: Rt 1.54 m/z 528.0 (MH⁺)

Example 29: (R)-4-(1-(4-(4-fluorophenoxy)-3'-(trifluoromethyl)-[1,1'-biphenyl]-3-carboxamido)ethyl) benzoic acid ¹H-NMR (400 MHz, DMSO-d⁶): δ=12.86 (s, 1H), 8.88 (d, 1H), 8.06 (m, 2H), 7.90 (t, 1H), 7.84 (dd, 3H), 7.72 (q, 2H), 7.45 (d, 2H), 7.25 (t, 2H), 7.12 (m, 2H), 7.03 (d, 1H), 5.13 (p, 1H), 1.40 (t, 3H).
HPLC-MS: Rt 2.45 m/z 524.0 (MH⁺)

Example 30: 4-(1-(4-(4-fluorophenoxy)-3'-(trifluoromethyl)-[1,1'-biphenyl]-3-carboxamido)cyclopropyl)benzoic acid ¹H-NMR (400 MHz, DMSO-d⁶): δ=9.09 (s, 1H), 8.04 (d, 2H), 7.95 (s, 1H), 7.86 (d, 1H), 7.73 (d, 4H), 7.27 (t, 2H), 7.18 (d, 2H), 7.13 (dd, 2H), 7.08 (d, 1H), 1.27 (t, 2H), 1.22 (t, 2H).
HPLC-MS: Rt 2.79 m/z 536.0 (MH⁺)

Example 31: 4-((3'-fluoro-5'-cyano-4-(4-fluorophenoxy)-[1,1'-biphenyl]-3-carboxamido) methyl)benzoic acid

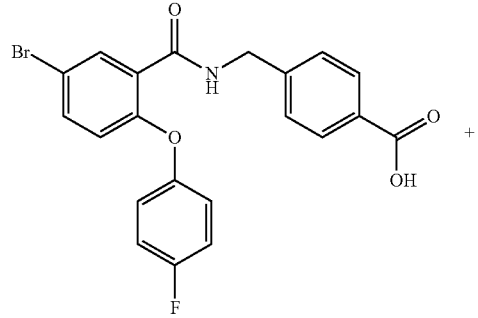

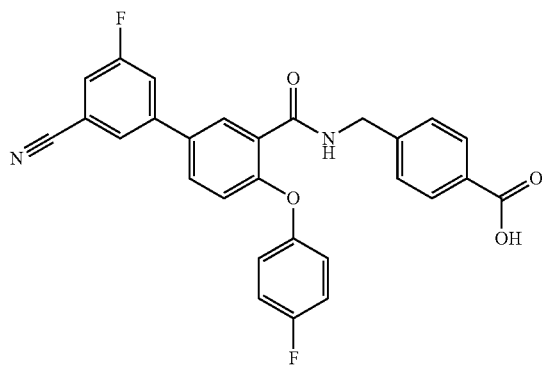

To a solution of 4-((5-bromo-2-(4-fluorophenoxy)benzamido)methyl)benzoic acid (80 mg, 1.0 eq) and (3-cyano-5-fluorophenyl)boronic acid (59 mg, 2.0 eq) in DMF (1.2 mL) 2M Cs2CO3 (0.27 mL, 3.0 eq) and Pd(dppf)Cl2·DCM (9 mg, 0.06 eq) under nitrogen atmosphere. After stirred at 110° C. for 20 h, the mixture was filtered through celite, rinsing with ethyl acetate (20 mL). The organic phase was washed with sat. aq. sodium bicarbonate (20 mL) and brine (20 mL), dried over Na2SO4, filtered and concentrated under reduced pressure. The crude material was purified by flash column chromatography (Hexanes:ethyl acetate, 1:1) to obtain the acid IV-484-536 as white solid (22 mg, 25.2% yield).

$^{1}$H-NMR (400 MHz, DMSO-d$^{6}$): δ=12.86 (s, 1H), 8.99 (t, 1H), 8.12 (s, 1H), 8.07 (d, 2H), 8.01 (dd, 1H), 7.89 (dd, 1H), 7.84 (d, 2H), 7.39 (d, 2H), 7.27 (m, 2H), 7.16 (m, 2H), 6.99 (d, 1H), 4.54 (d, 2H).

HPLC-MS: Rt 2.23 m/z 485.1 (MH$^{+}$)

Example 32: 4-((3'-chloro-5'-cyano-4-(4-fluorophenoxy)-[1,1'-biphenyl]-3-carboxamido) methyl)benzoic acid

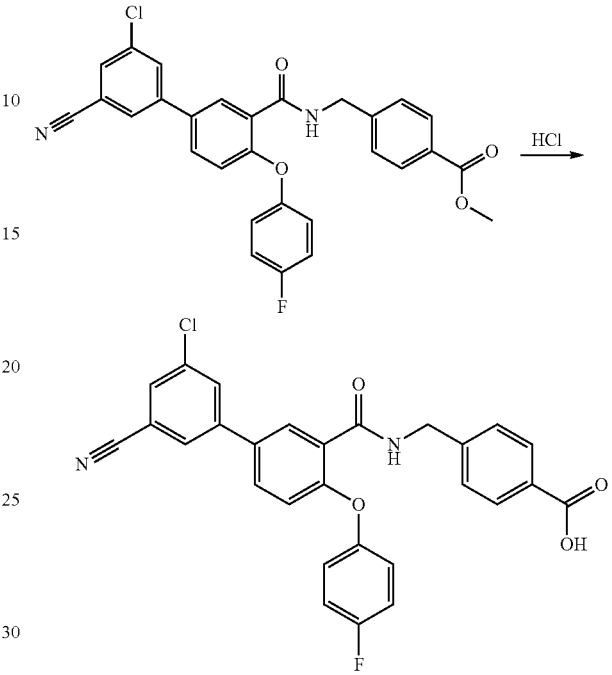

To a solution of methyl 4-((3'-cyano-5'-fluoro-4-(4-fluorophenoxy)-[1,1'-biphenyl]-3-ylcarboxamido)methyl)benzoate (100 mg, 1.0 eq) in THF (1.0 mL) was added HCl (4 M) (3.0 mL) and the mixture was stirred for 46 hours at 80° C. After diluting with water (5 mL), the mixture was extracted with ethyl acetate (3×10 mL), dried over Na2SO4, filtered and concentrated under reduced pressure. The crude material was purified by flash column chromatography (Hexanes:ethyl acetate, 1:1) to obtain the acid as white solid (18 mg, 18.6% yield).

$^{1}$H-NMR (400 MHz, DMSO-d$^{6}$): δ=12.87 (s, 1H), 8.98 (t, 1H), 8.22 (s, 1H), 8.16 (t, 1H), 8.07 (d, 1H), 8.03 (m, 1H), 7.89 (dd, 1H), 7.84 (d, 2H), 7.39 (d, 2H), 7.27 (m, 2H), 7.16 (m, 2H), 6.99 (d, 1H), 4.54 (d, 2H).

HPLC-MS: Rt 2.34 m/z 501.1 (MH$^{+}$)

The invention claimed is:
1. A compound of formula (I):

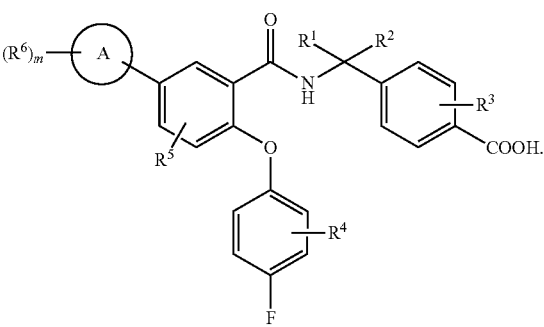

wherein:
A represents a group selected from phenyl and five or six-membered heteroaryl containing one, two or three heteroatoms selected from N, S and O,
$R^1$ and $R^2$ represent independently a group selected from hydrogen atom, halogen atom and $C_{1-3}$ alkyl, or $R^1$ and $R^2$ together with the carbon atom to which they are attached form a $C_{3-4}$ cycloalkyl group,
$R^3$, $R^4$, $R^5$ and each $R^6$ represent independently a group selected from hydrogen atom, halogen atom, cyano group, carbamoyl group, linear or branched $C_{1-3}$ haloalkyl group, linear or branched $C_{1-3}$ alkyl, $C_{3-4}$ cycloalkyl, linear or branched $C_{1-3}$ alkoxy and a pyridyl group,
m is an integer from 1 to 5,
and pharmaceutically acceptable salts thereof.

2. A compound according to claim 1 wherein $R^1$, $R^2$, $R^3$, $R^4$ and $R^5$ represent hydrogen atoms.

3. A compound according to claim 1 wherein A represents a phenyl group.

4. A compound according to claim 3 wherein each $R^6$ independently represents a group selected from:
a) hydrogen atom,
b) halogen atom
c) cyano group,
d) carbamoyl group
e) linear or branched $C_{1-3}$ haloalkyl group.

5. A compound according to claim 1 wherein A represents a phenyl group and each $R^6$ independently represents a group selected from fluoro, trifluoromethyl and cyano group, and m is an integer from 1 to 4.

6. A compound according to claim 1 wherein A represents a five or six-membered heteroaryl ring.

7. A compound according to claim 6 wherein A represents a group selected from a pyridinyl or a thiophenyl groups, each $R^6$ independently represents a group selected from trifluoromethyl and cyano groups and m is an integer from 1 to 4.

8. A compound according to claim 1 wherein $R^1$, $R^2$, $R^3$, $R^4$ and $R^5$ represent hydrogen atoms, A represents a phenyl group and each $R^6$ independently represent a group selected from fluoro and trifluoromethyl groups and m is an integer from 1 to 5.

9. A compound according to claim 1 wherein m is an integer from 1 to 2.

10. A compound according to claim 1 wherein A represents a group selected from phenyl, pyridinyl, pyrimidinyl, tiophenyl, $R^1$, $R^2$, $R^3$, $R^4$, $R^5$ are hydrogen atoms, each $R^6$ represents independently a group selected from hydrogen atom, fluorine, chlorine, cyano group, trifluoromethyl and pyridinyl group and m is and integer from 1 to 2.

11. A compound according to claim 1 which is one of:
4-((2-(4-fluorophenoxy)-5-(pyridin-4-yl)benzamido)methyl)benzoic acid
4-((4-(4-fluorophenoxy)-[1,1'-biphenyl]-3-carboxamido)methyl)benzoic acid
4-((4'-chloro-4-(4-fluorophenoxy)-[1,1'-biphenyl]-3-carboxamido)methyl)benzoic acid
4-((4'-fluoro-4-(4-fluorophenoxy)-[1,1'-biphenyl]-3-carboxamido)methyl)benzoic acid
4-((3'-fluoro-4-(4-fluorophenoxy)-[1,1'-biphenyl]-3-carboxamido)methyl)benzoic acid
4-((2'-fluoro-4-(4-fluorophenoxy)-[1,1'-biphenyl]-3-carboxamido)methyl)benzoic acid
4-((4'-cyano-4-(4-fluorophenoxy)-[1,1'-biphenyl]-3-carboxamido)methyl)benzoic acid
4-((3'-cyano-4-(4-fluorophenoxy)-[1,1'-biphenyl]-3-carboxamido)methyl)benzoic acid
4-((2-(4-fluorophenoxy)-5-(3-fluoropyridin-4-yl)benzamido)methyl)benzoic acid)
4-((2-(4-fluorophenoxy)-5-(pyridin-3-yl)benzamido)methyl)benzoic acid
4-((2-(4-fluorophenoxy)-5-(3-chloropyridin-4-yl)benzamido)methyl)benzoic acid
4-((2-(4-fluorophenoxy)-5-(pyrimidin-5-yl)benzamido)methyl)benzoic acid
4-((3',4'-difluoro-4-(4-fluorophenoxy)-[1,1'-biphenyl]-3-carboxamido)methyl)benzoic acid
4-((4-(4-fluorophenoxy)-4'-(trifluoromethyl)-[1,1'-biphenyl]-3-carboxamido)methyl)benzoic acid
4-((4-(4-fluorophenoxy)-3'-(trifluoromethyl)-[1,1'-biphenyl]-3-carboxamido)methyl)benzoic acid
4-((2-(4-fluorophenoxy)-5-(pyridin-2-yl)benzamido)methyl)benzoic acid
4-((2-(4-fluorophenoxy)-5-(pyrimidin-4-yl)benzamido)methyl)benzoic acid
4-((2-(4-fluorophenoxy)-5-(thiophen-2-yl)benzamido)methyl)benzoic acid
4-((3',5'-difluoro-4-(4-fluorophenoxy)-[1,1'-biphenyl]-3-carboxamido)methyl))benzoic acid
4-((3'-chloro-4-(4-fluorophenoxy)-[1,1'-biphenyl]-3-carboxamido)methyl)benzoic acid
4-((3'-fluoro-4-(4-fluorophenoxy)-5'-(trifluoromethyl)-[1,1'-biphenyl]-3-carboxamido)methyl)benzoic acid
4-((3'-carbamoyl-5'-chloro-4-(4-fluorophenoxy)-[1,1'-biphenyl]-3-ylcarboxamido)methyl)benzoic acid
4-((2-(4-fluorophenoxy)-5-(1H-pyrazol-4-yl)benzamido)methyl)benzoic acid
4-((2-(4-fluorophenoxy)-5-(1-methyl-1H-pyrazol-4-yl)benzamido)methyl)benzoic acid
4-((2-(4-fluorophenoxy)-5-(1-methyl-1H-pyrazol-5-yl)benzamido)methyl)benzoic acid
4-((4-(4-fluorophenoxy)-3'-(pyridin-4-yl)-[1,1'-biphenyl]-3-ylcarboxamido)methyl)benzoic acid
4-((5-(5-carbamoylfuran-2-yl)-2-(4-fluorophenoxy)benzamido)methyl)benzoic acid
3-fluoro-4-((4-(4-fluorophenoxy)-3'-(trifluoromethyl)-[1,1'-biphenyl]-3-ylcarboxamido)methyl)benzoic acid
(R)-4-(1-(4-(4-fluorophenoxy)-3'-(trifluoromethyl)-[1,1'-biphenyl]-3-carboxamido)ethyl)benzoic acid
4-(1-(4-(4-fluorophenoxy)-3'-(trifluoromethyl)-[1,1'-biphenyl]-3-carboxamido)cyclopropyl)benzoic acid
4-((3'-fluoro-5'-cyano-4-(4-fluorophenoxy)-[1,1'-biphenyl]-3-carboxamido)methyl)benzoic acid
4-((3'-chloro-5'-cyano-4-(4-fluorophenoxy)-[1,1'-biphenyl]-3-carboxamido)methyl)benzoic acid
and pharmaceutically acceptable salts thereof.

12. A method of treatment of diseases or pathological condition that can be ameliorated by modulation of EP4 and/or EP2 receptors of prostaglandin E2 (PGE2), wherein said disease or pathological condition is selected from the group consisting of cancer, pain, neurodegenerative diseases, osteoarthritis, rheumatoid arthritis, endometriosis and kidney diseases, said method comprising administering an effective amount of a compound according to claim 1 to a subject in need thereof.

13. A method of treatment of cancer, wherein the cancer is amenable to be treated with immunotherapy, said method comprising administering an effective amount of a compound according to claim 1 to a subject in need thereof.

14. A pharmaceutical composition comprising a compound according to claim 1, a pharmaceutically acceptable diluent or carrier and optionally a therapeutically effective amount of further chemotherapeutics agents, anti-inflammatory agents, steroids, immunotherapeutic agent and other agents such as therapeutic antibodies.

15. A combination product comprising a compound according to claim 1 or a pharmaceutically acceptable salt thereof and at least a therapeutic agent selected from the group consisting of chemotherapeutics agents, anti-inflammatory agents, steroids, immunosuppressants, immunotherapeutic agents, therapeutic antibodies and EP4 and/or EP2 modulators, in particular those selected from the group consisting of antibodies anti-CTLA4, selected from Ipilimumab and tremelimumab, antibodies anti-PD1 such as nivolumab, pembrolizumab, cemiplimab, pidilizumab, spartalizumab, MEDI0680, REGN2810 and AMP-224, antibodies anti-POL1 such as Atezolizumab, Avelumab, Durvalumab, and MDX-1105; Carboplatin, Carmustine (BCNU), Cisplatin, Cyclophosphamide, Etoposide, Irinotecan, Lomustine (CCNU), Methotrexate, Procarbazine, Temozolomide, Vincristine.

* * * * *